United States Patent
Miyazawa et al.

(10) Patent No.: US 6,326,011 B1
(45) Date of Patent: Dec. 4, 2001

(54) COPOLYMER CONTAINING REACTIVE SILYL GROUPS, COMPOSITION CONTAINING THE SAME AND METHOD OF TREATMENT WITH THE SAME

(75) Inventors: Kazuyuki Miyazawa; Toshio Yanaki; Fumiaki Matsuzaki, all of Kanagawa (JP)

(73) Assignee: Shiseido Co., Ltd., Tokyo (JP)

( * ) Notice: Subject to any disclaimer, the term of this patent is extended or adjusted under 35 U.S.C. 154(b) by 0 days.

(21) Appl. No.: 09/230,582

(22) PCT Filed: Jun. 1, 1998

(86) PCT No.: PCT/JP98/02407

§ 371 Date: Jan. 26, 1999

§ 102(e) Date: Jan. 26, 1999

(87) PCT Pub. No.: WO98/54255

PCT Pub. Date: Dec. 3, 1998

(30) Foreign Application Priority Data

| May 30, 1997 | (JP) | 9-157675 |
| Aug. 29, 1997 | (JP) | 9-249547 |
| Aug. 29, 1997 | (JP) | 9-249548 |
| Oct. 20, 1997 | (JP) | 9-306442 |
| Feb. 20, 1998 | (JP) | 10-055751 |
| Feb. 20, 1998 | (JP) | 10-055752 |
| Feb. 20, 1998 | (JP) | 10-055753 |
| May 30, 1998 | (JP) | 9-157676 |
| May 30, 1998 | (JP) | 9-157677 |

(51) Int. Cl.$^7$ ............... A61K 6/00; A61K 7/00

(52) U.S. Cl. .......... 424/401; 424/400; 424/70.1; 424/70.6; 424/70.7; 424/70.12; 424/70.13; 424/78.08; 424/78.31; 424/78.35; 424/78.37; 424/63; 424/402; 528/25; 528/26; 528/28; 528/32; 528/33; 528/34; 528/39

(58) Field of Search ................... 424/70.1, 401, 424/70.12, 70.13, 78.08, 78.18, 78.31, 78.35, 78.37, 63, 70.6; 8/495; 427/452; 528/25, 26, 28, 32, 33, 34, 39

(56) References Cited

U.S. PATENT DOCUMENTS

| 3,453,230 | * | 7/1969 | Plueddemann | 260/41 |
| 4,450,264 | * | 5/1984 | Cho | 526/279 |
| 5,688,493 | * | 11/1997 | Sugawara et al. | 424/61 |
| 5,705,561 | * | 1/1998 | Kozakiewicz et al. | 524/730 |
| 5,708,048 | * | 1/1998 | Medford et al. | 522/64 |

FOREIGN PATENT DOCUMENTS

10029915A * 2/1998 (JP) .

OTHER PUBLICATIONS

Dow Corning Corporation. Chapter 11 Information. Facts about Dow Corning. pp. 1–4.*

Merriam Webster's Collegiate Dictionary. Tenth Edition. p. 256.*

* cited by examiner

Primary Examiner—Thurman K. Page
Assistant Examiner—Liliana Di Nola-Baron
(74) Attorney, Agent, or Firm—Snider & Associates; Ronald R. Snider

(57) ABSTRACT

A copolymer having silyl groups with at least one reactive functional group bonded thereto. The copolymer comprises a monomer (A) shown by the following Formula (I):

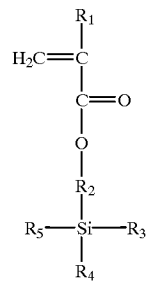

wherein $R_1$ is hydrogen atom or methyl; $R_2$ is alkylene group having 1–6 carbon atoms; and $R_3$, $R_4$ and $R_5$ each is a reactive functional group which can cross-link molecules of the copolymer by hydrolyzing. Further, the copolymer preferably comprises, as a constituent monomer, an alkyl (meth) acrylate and a siloxane-containing (meth)acrylate. A coating-forming method comprises hydrolyzing the composition on a material to be treated to cross-link molecules of the copolymer when on the material. A coating of the cross-linked copolymer has resistance to washing. This coating can modify the nature of hair, improve make-up retention, and provide skin-protecting. It can impart water-repellency, resistance to fouling, suitability as a sizing and crease resistance to fibers. Further, it can improve a skin-cleaning effect, applicability, strippability and coating-strength of a peeling-off type cosmetic pack.

24 Claims, 5 Drawing Sheets

COPOLYMER CONTAINING REACTIVE SILYL GROUPS, COMPOSITION CONTAINING THE SAME AND METHOD OF TREATMENT WITH THE SAME

RELATED APPLICATIONS

This application claims the priority of Japanese Patent Application Nos. 9-157675, 9-157676 and 9-157677 filed on May 30, 1997, Japanese Patent Application Nos. 10-55751, 10-55752 and 10-55753 filed on Feb. 20, 1998, Japanese Patent Application Nos. 9-249547 and 9-249548 filed on Aug. 29, 1997, and Japanese Patent Application No. 9-306442 filed on Oct. 20, 1997, which are incorporated herein by reference.

FIELD OF THE INVENTION

The present invention relates to a copolymer containing reactive silyl groups, a composition comprising the same, and a treating method using the same. Particularly, the present invention relates to: a copolymer, which forms a strong coating of the cross-linked copolymer which has resistance to washing on the surface of hair, skin or other materials. The invention is useful effects in the fields of cosmetics and the others. It had a modifying effect of the nature of hair, improves the effect of make-up retention and has a water-repellent effect.

BACKGROUND OF THE INVENTION

Numerous film-forming ingredients are used in the field of cosmetics and the other fields for the purpose of giving various effects.

However, there are very few film-forming ingredients that have a useful effect as a cosmetic ingredient and which maintain the effect against washing with shampoo or detergent.

Also, in the field where water-repellents give water-repellency to fibers, paper or the other materials, it is expected to improve resistance to washing.

SUMMARY OF THE INVENTION

The first object of the present invention is to find a compound that can form a coating, wherein said coating can exhibit cosmetically useful effects such as a hair-nature modifying effect, an improving effect of the retention of hair colorants or make-up cosmetics, and skin-protecting effect. These effects are maintained due to a high resistance to washing. It is a further object to provide a composition comprising the compound.

Also, the second object of the present invention is to find a compound that can form a coating, which is excellent in water-repellency and resistance to washing when on materials to be treated such as fibers. It is a further object to provide a composition comprising the compound.

It has been found that a strong coating of a cross-inked copolymer that is excellent in resistance to washing can be formed when a copolymer containing a silyl group that one or more reactive functional groups are bonded to (e.g., a trifunctional silyl group) is crosslinked with hydrolysis on the material to be treated such as hair or skin.

Also, it has been found that such cross-linked coating has a hair-nature modifying effect and a skin-protecting effect, and these effects are maintained without loss even with repeated shampooing.

Also, it has been found that the cross-linked coating formed by such copolymer ameliorates resistance to washing off of make-up cosmetics such as temporary hair colorant, acidic hair dye, mascara or nail enamel and improves make-up retention.

Also, it has been found that a cosmetic pack comprising the copolymer has a good skin-cleaning characteristic and is excellent in applicability, strippability and film strength.

Further, a coating which has high water-repellency, resistance to fouling and suitability as a sizing and which is excellent in resistance to washing can be formed even when the copolymer is treated on other materials such as fibers, paper or glass.

A composition of the present invention comprises a copolymer containing silyl groups wherein each silyl group has at least one reactive functional group bonded thereto.

The silyl group has at least one reactive functional group bonded thereto that can cross-link molecules of the copolymer by forming a siloxane bond Si—O—Si with hydrolysis.

Also it is preferable that, as one of the constituent monomers, the copolymer comprises Monomer (A) shown by the following Formula (I):

Formula (I)

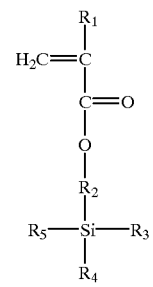

wherein R is a hydrogen atom or methyl group; $R_2$ is an alkylene group having 1–6 carbon atoms; and $R_3$, $R_4$ and $R_5$ each is a reactive functional group which can cross-link molecules of the copolymer hydrolyzing.

Also, it is preferable that, as one of the constituent monomers, the copolymer further comprises Monomer (B) shown by the following Formula (II):

Formula (II)

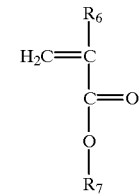

wherein $R_6$ is a hydrogen atom or methyl group; and $R_7$ is an alkyl group having 1–18 carbon atoms.

Also, it is preferable that as one of the constituent monomers, the copolymer further comprises Monomer (C) shown by the following Formula (III):

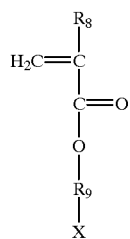

Formula (III)

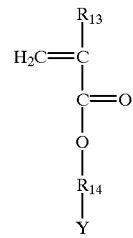

Formula (VII)

wherein $R_8$ is a hydrogen atom or methyl group; $R_9$ is an alkylene group having 1–6 carbon atoms; and X is any of groups shown by the following Formulas (IV) to (VI):

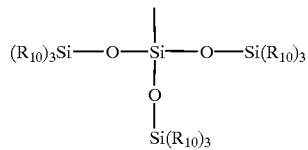

Formula (IV)

wherein $R_{10}$ is an all group having 1–6 carbon atoms;

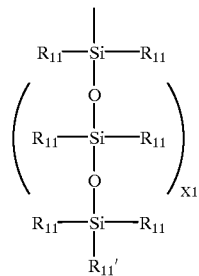

Formula (V)

wherein $R_{11}$ and $R_{11}'$ each is an alkyl group having 1–6 carbon atoms; and x1 is an integer of positive number; and

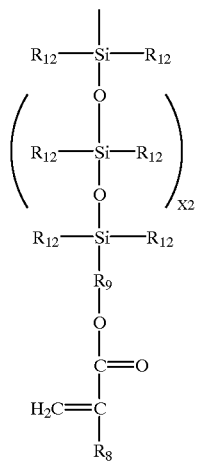

Formula (VI)

wherein $R_8$ and $R_9$ can be the same as defined in Formula (III); $R_{12}$ is an alkyl group having 1–6 carbon atoms; and x2 is an integer of positive number.

It is preferable that the percentage of Monomer (A) in the copolymer is 25 to 99 wt %.

Also, it is preferable that the percentage of Monomer (B) in the copolymer is 1 wt % or more.

Also, it is preferable that the percentage of Monomer (C) in the copolymer is 1 wt % or more.

Also, the copolymer can further comprise a constituent Monomer (D) shown by the following Formula (VII):

wherein $R_{13}$ is a hydrogen atom or methyl group; $R_{14}$ is an alkylene group having 1–6 carbon atoms; and Y is a group shown by $-N^+(R_{15})_3$ or $-N(R_{15})_2$, and wherein $R_{15}$ is an alkyl group having 1–6 carbon atoms.

It is preferable that the percentage of Monomer (D) in the copolymer is within the range of 1 to 100 wt % with respect to the combined amount of Monomers (A), (B) and (C) in the copolymer.

Also, it is preferable that $R_3$, $R_4$ and $R_5$ are each an alkoxy group having 1–6 carbon atoms.

A cosmetic for coating in accordance with the present invention is a composition comprising any of said copolymers.

A cosmetic for modifying the nature of hair in accordance with the present invention is a composition comprising any of said copolymers.

A hair colorant in accordance with the present invention is a composition comprising any of said copolymers together with a pigment and/or an acidic dye.

A cosmetic in accordance with the present invention is a composition comprising any of said copolymers together with a pigment and/or an acidic dye.

A make-up cosmetic in accordance with the present invention is a composition comprising any of said copolymers together with a pigment and/or an acidic dye.

Also, in any of said cosmetics, a siliconized polysaccharide can be further used therein.

A cosmetic pack in accordance with the present invention is a composition comprising any of said copolymers.

A water-repellent in accordance with the present invention is a composition comprising a copolymer containing at least Monomer (A) shown by Formula (I), Monomer (B) shown by Formula (II) and Monomer (C) shown by Formula (III) as constituent monomers.

In the water-repellent of the present invention, it is preferable that the percentage of Monomer (A) in the copolymer is 25 to 85 wt %. It is also preferable that the percentage of Monomer (B) in the copolymer is 5 wt % or more and the percentage of Monomer (C) in the copolymer is 1 wt % or more.

A treatment for fibers in accordance with the present invention is a composition comprising a copolymer which contains Monomer (A) shown by Formula (I), Monomer (B) shown by Formula (II), and Monomer (C) shown by Formula (III) as constituent monomers.

In the treatment for fibers of the present invention, it is preferable that the percentage of Monomer (A) in the copolymer is 25 to 85 wt %. It is also preferable that the percentage of Monomer (B) in the copolymer is 5 wt % or more and the percentage of Monomer (C) in the copolymer is 1 wt % or more.

A copolymer in accordance with the present invention comprises Monomer (A) shown by Formula (I), Monomer (B) shown by Formula (II) and Monomer (C) shown by Formula (III) as constituent monomers.

A copolymer in accordance with the present invention comprises Monomer (A) shown by Formula (I), Monomer (B) shown by Formula (II), Monomer (C) shown by Formula (III) and Monomer (D) shown by Formula (VII) as constituent monomers.

In the copolymer of the present invention, $R_3$, $R_4$ and $R_5$ are each an alkoxy group having 1 to 6 carbon atoms.

A coating-forming method in accordance with the present invention comprises a step of hydrolyzing said compositions on the materials to be treated to cross-link molecules of the copolymer.

In the method of the present invention, it is preferable that the composition is any of said cosmetics and the material to be treated is human hair or epidermis.

Also, in the method of the present invention, it is preferable that the composition is any of said water-repellents and the material to be treated is fibers, paper or glass.

A method for applying a cosmetic pack in accordance with the present invention comprises steps of: hydrolyzing said cosmetic pack on skin to cross-link molecules of the copolymer, and peeling the cosmetic pack from the skin after drying.

BEST MODE FOR CARRYING OUT THE INVENTION

Figure 1:
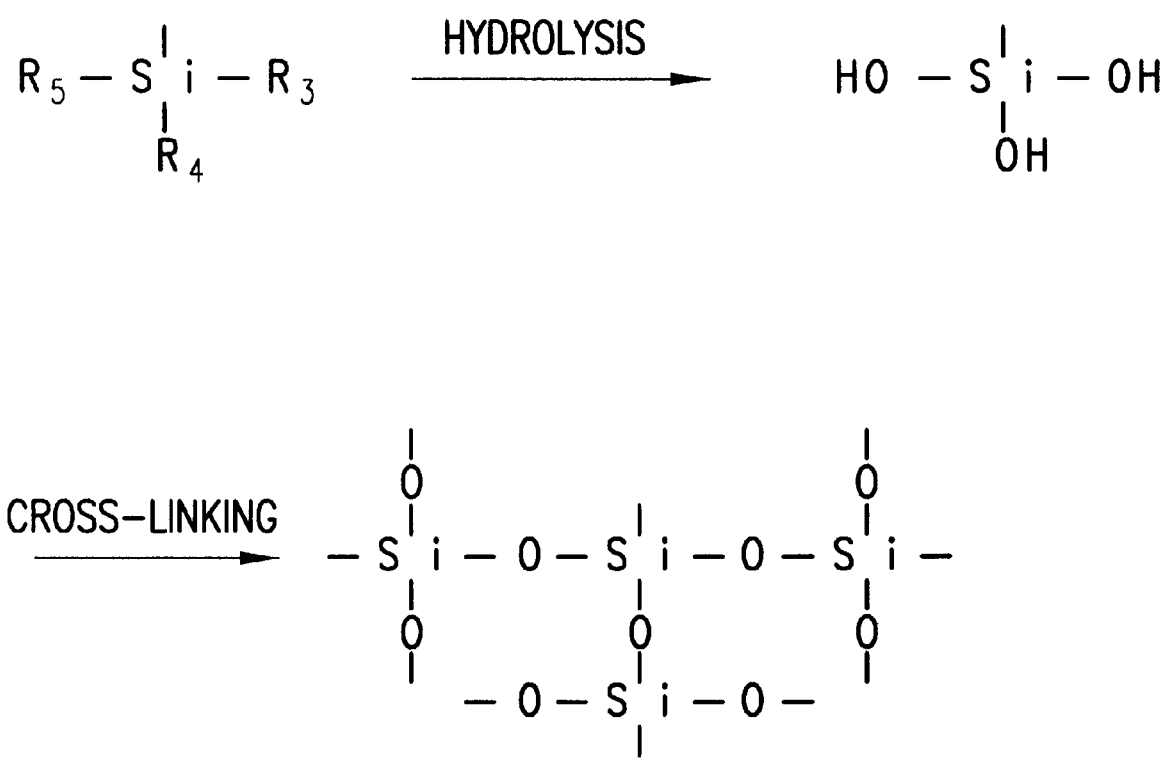
FIG. 1 shows one example of cross-linking reaction of the copolymer in accordance with the present invention.
Figure 2:
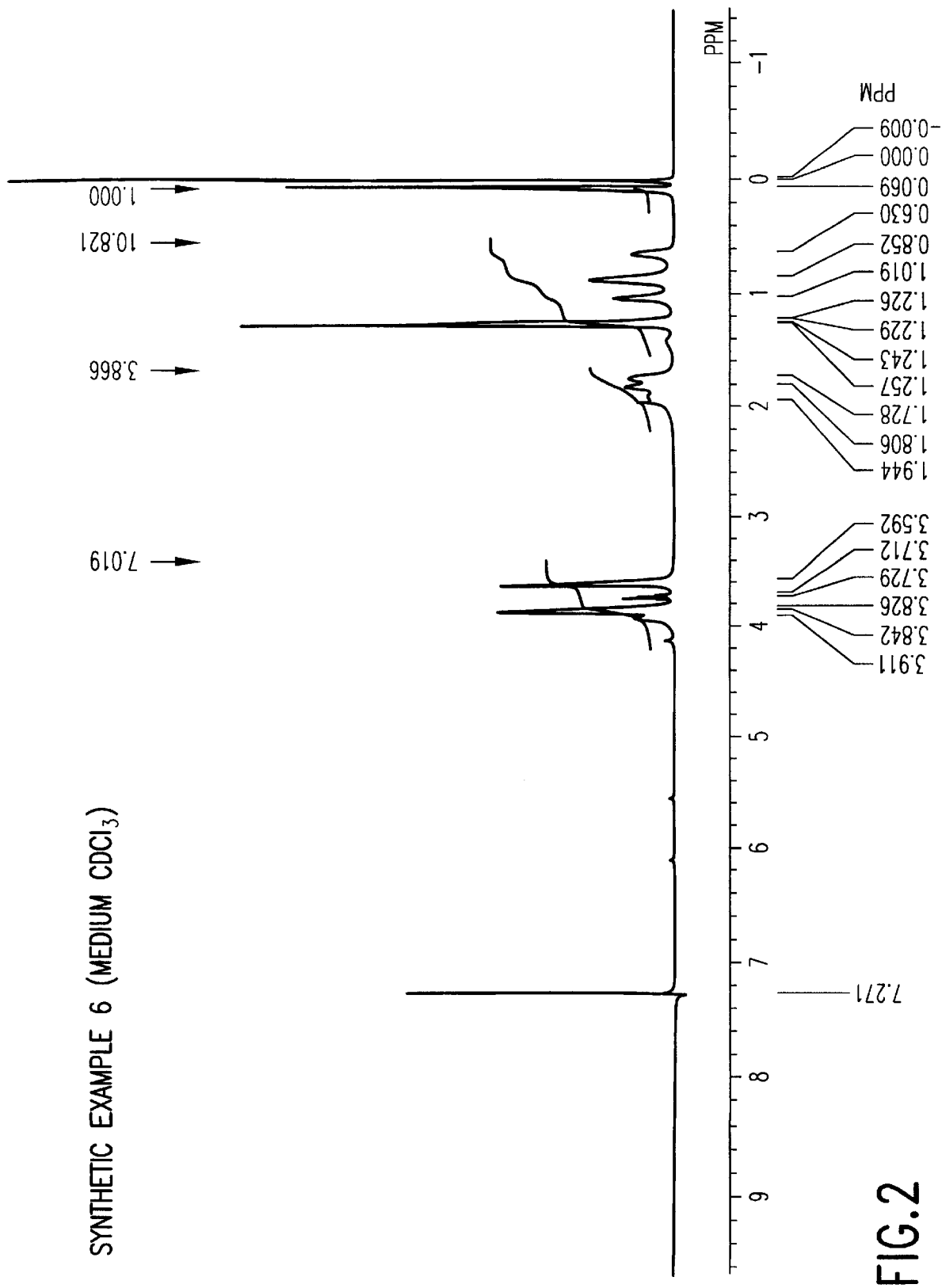
FIG. 2 shows an NMR spectrum of Synthetic Example 6 (Medium $CDCl_3$).
Figure 3:
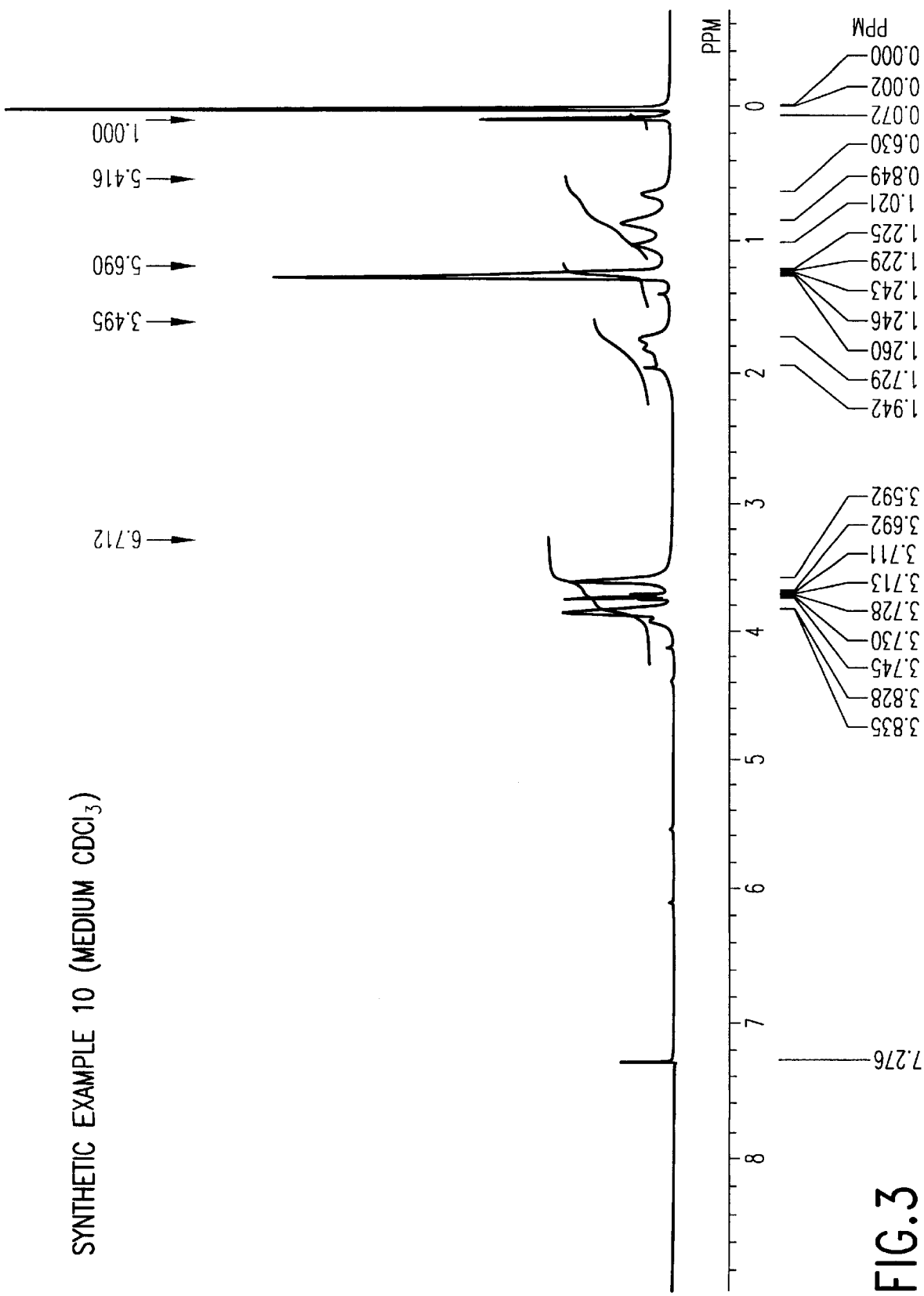
FIG. 3 shows an NMR spectrum of Synthetic Example 10 (Medium $CDCl_3$).
Figure 4:
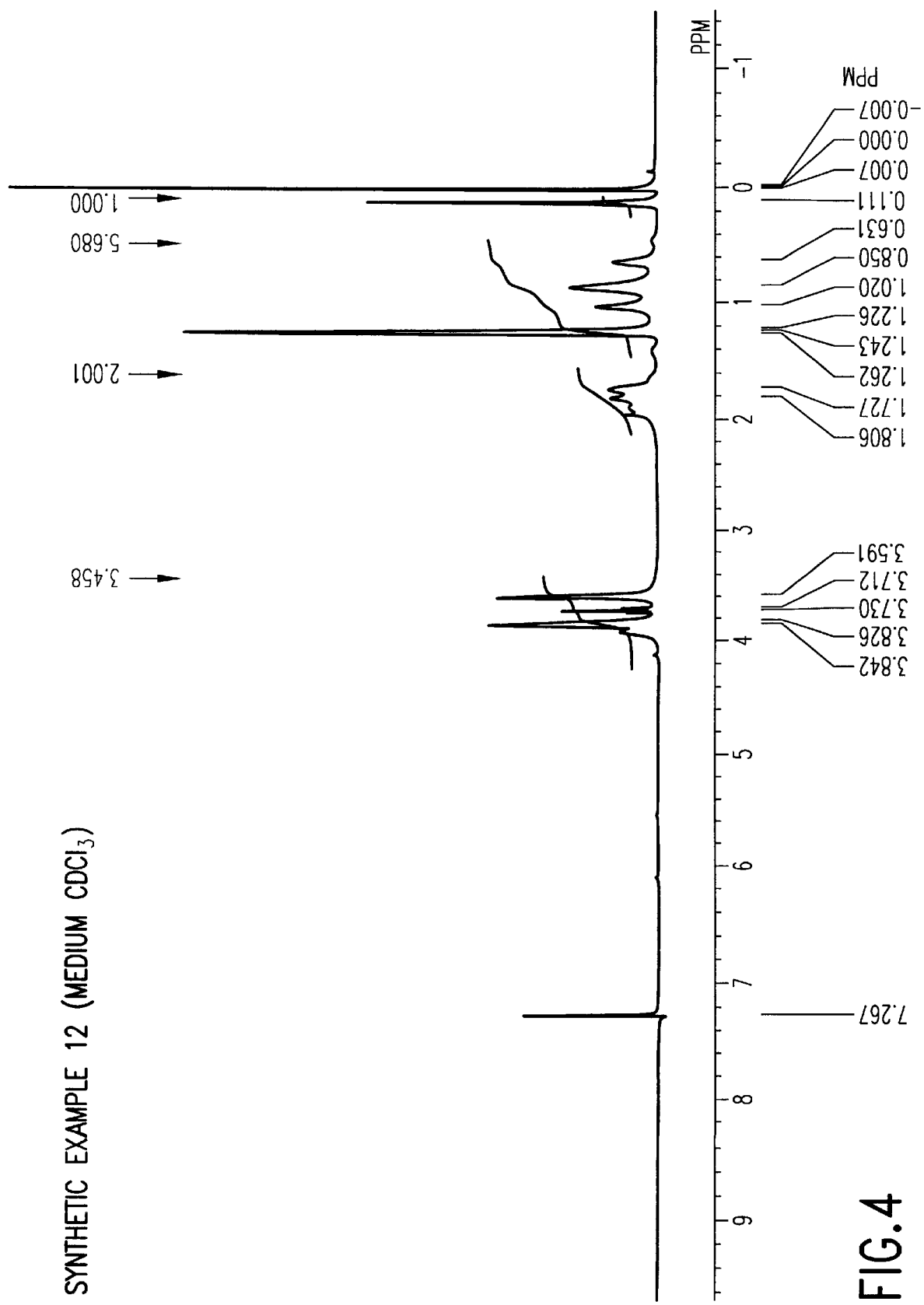
FIG. 4 shows an NMR spectrum of Synthetic Example 12 (Medium $CDCl_3$).
Figure 5:
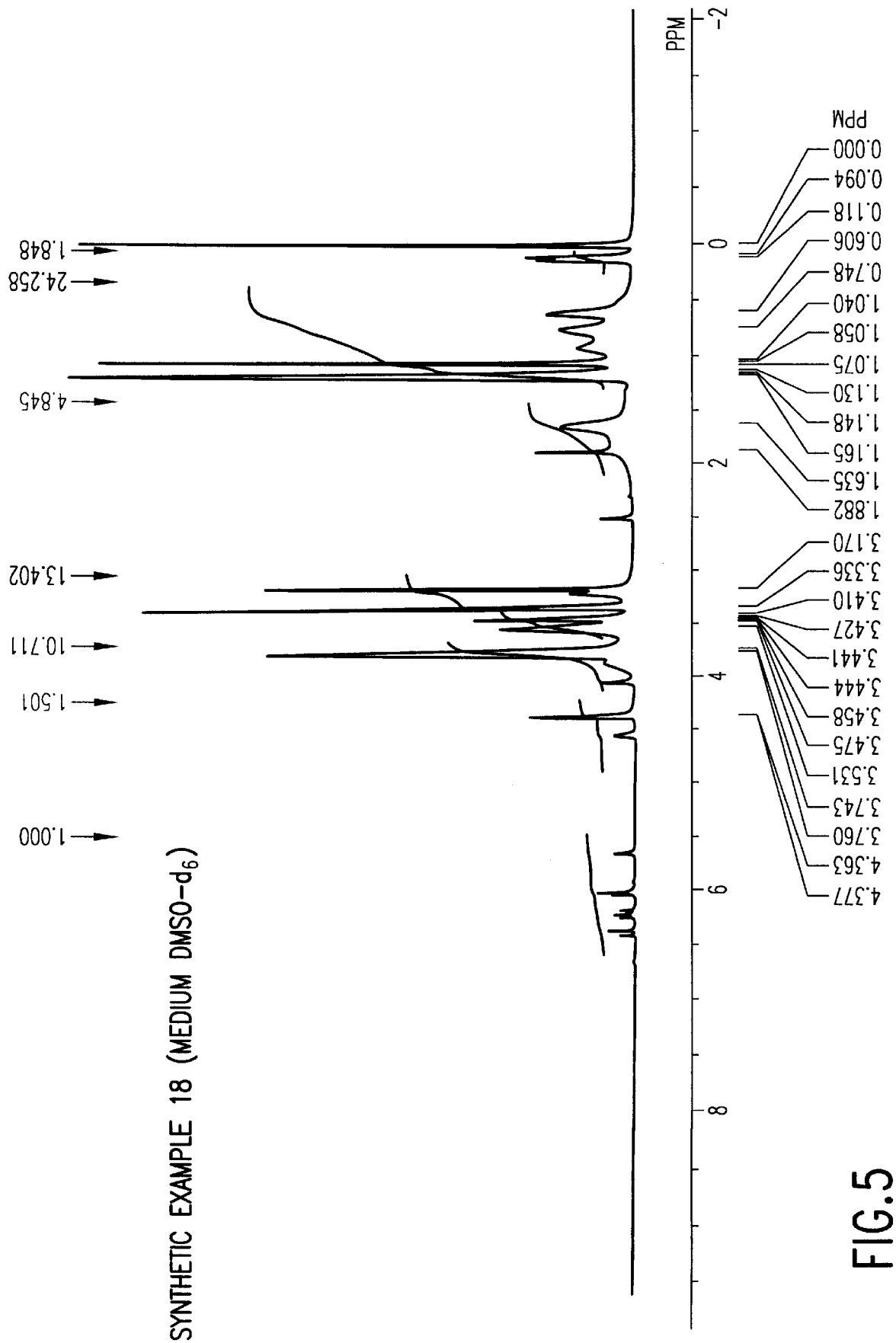
FIG. 5 shows an NMR spectrum of Synthetic Example 18 (Medium $DMSO-d_6$).

In the following, the embodiments for carrying out the present invention will be explained.

The copolymer comprised in the composition of the present invention contains silyl groups having at least one reactive functional group bonded thereto.

Preferable examples of the copolymer include a copolymer having mono- to tri- functional silyl groups. A copolymer comprising trifunctional silyl groups is more preferable.

One of the preferable copolymers of the present invention can be a copolymer comprising Monomer (A) shown by Formula (I) as a constituent monomer.

Monomer (A) is an acrylate or methacrylate comprising a trifunctional silyl group $—SiR_3R_4R_5$. $R_1$ is a hydrogen atom or methyl group in Formula (I). Also, $R_2$ is an alkylene group having 1 to 6 carbon atoms and preferably, is propylene group.

$R_3$, $R_4$, and $R_5$, are each a reactive functional group, which can cross-link molecules of the copolymer of the present invention due to forming a siloxane bond Si—O—Si by hydrolysis. Examples of such a functional group include a hydrogen atom, alkoxy group, halogen atom, acyloxy group and amino group. An alkoxy group having 1 to 6 carbon atoms is preferable in terms of stability of the copolymer, safety of byproduct formed by hydrolysis, reactivity of the cross-linking reaction mentioned later, and the like. Methoxy or ethoxy group is more preferable. Also, $R_3$, $R_4$, and $R_5$ each may be the same or different. In the copolymer of the present invention, at least one of Monomer (A) can be used as a constituent monomer.

Preferably in terms of effect, the copolymer of the present invention comprises the other constituent monomers along with the monomer containing the reactive silyl group such as Monomer (A). Although various monomers may be considered as a constituent monomer, Monomer (B) shown by the foregoing Formula (II) can be a preferable example.

Monomer (B) is an alkyl acrylate or alkyl methacrylate. In Formula (II), $R_6$ is a hydrogen atom or methyl group. $R_7$ is a straight, branched or cyclic alkyl group having 1 to 18 carbon atoms. However, $R_7$ is preferably an alkyl group having 1 to 6 carbon atoms and, more preferably, methyl group. In the copolymer of the present invention, at least one of the foregoing Monomer (B) can be used as a constituent monomer.

Also, in the copolymer of the present invention, it is preferable to comprise Monomer (C) of the foregoing Formula (II) as a constituent monomer. Monomer (C) is siloxane-containing (meth)acrylate. $R_8$ is a hydrogen atom or methyl group in Formula (III). $R_9$ is an alkylene group having 1 to 6 carbon atoms and, preferably, ethylene, propylene or 2-hydroxypropylene group. X is a siloxane expressed by any of the foregoing Formulas (IV) to (VI). $R_{10}$, $R_{11}$, $R_{12}'$ and $R_{12}$ each is a straight or branched alkyl group having 1 to 6 carbon atoms or phenyl group in Formulas (IV) to (VI). Although $R_{10}$, $R_{11}$ and $R_{12}$ each exist plurally in these formulas, they may be the same or different from each other. Methyl group is preferable as $R_{10}$, $R_{11}$ and $R_{12}$. Butyl group is preferable as $R_{11}'$. A molecular weight of Monomer (C) is 1,000 to 100,000 and, preferably, 2,000 to 20,000 when X is Formula (V) or (VI). Also, in the copolymer of the present invention, at least one of the foregoing Monomer (C) can be used as a constituent monomer.

The copolymer of the present invention can further comprise amine-containing (meth)acrylate Monomer (D) shown by the foregoing Formula (VII). $R_{13}$ is a hydrogen atom or methyl group in Formula (VII). $R_{14}$ is an alkylene group having 1 to 6 carbon atoms and, preferably, ethylene or propylene group. Y is a group shown by $—N^+(R_{15})_3$ or $—N(R_{15})_2$, and $R_{15}$ is an alkyl group having 1 to 6 carbon atoms. Also, Y may be a salt whose counter ion is halogen, inorganic acid, organic acid or the like, when Y is the group of $—N^+(R_{15})_3$.

Also, the copolymer of the present invention can comprise Monomer (E) as a constituent monomer which is not the above-mentioned Monomers (A) to (D) as long as the effect of the present invention is not destroyed.

A preferable example of the copolymer comprised in the composition of the present invention can be, for example, a copolymer shown by the following Formulas (VIII, (IX) or (X):

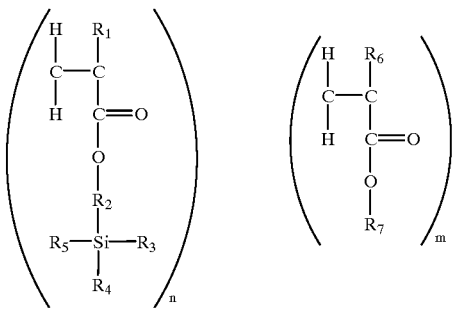

Formula (VIII)

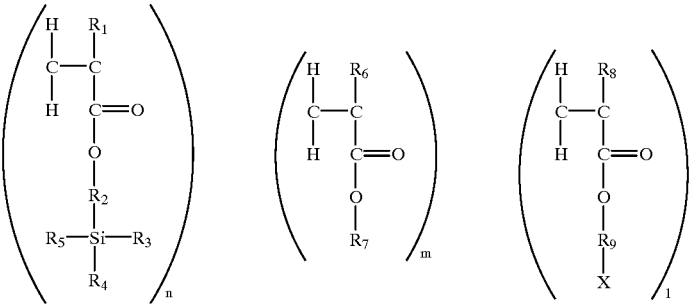

Formula (IX)

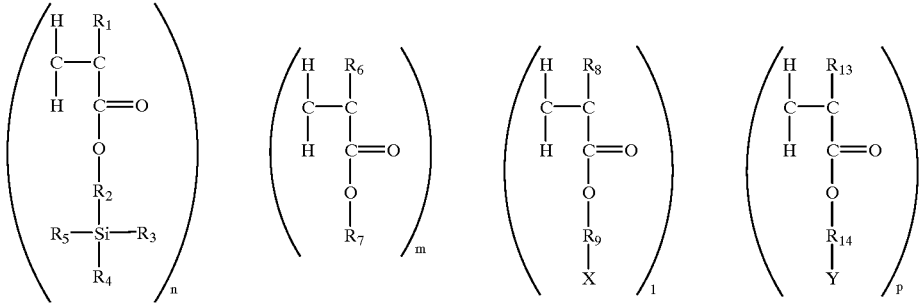

Formula (X)

wherein $R_1$, $R_2$, $R_3$, $R_4$, $R_5$, $R_6$, $R_7$, $R_8$, $R_9$, $R_{13}$, $R_{14}$, X and Y are the same as defined in the above, and n, m, l, and p are molar ratios of Monomers (A), (B), (C) and (D), respectively.

The copolymer in accordance with the present invention can be obtained by polymerizing the foregoing monomers by means of a known polymerization method such as the solution polymerization method, the emulsion polymerization method or the bulk polymerization method. For example, in the case of the solution polymerization method, the copolymer of the present invention can be obtained by dissolving each monomer in a solvent with the desired monomer ratio, adding a radical polymerization initiator under nitrogen atmosphere, and heating while stirring.

As a solvent used in polymerization, it is possible to use any solvent that can dissolve or suspend the monomers. An organic solvent which does not comprise water can be used. For example, in addition to alcohol type solvents such as methanol, ethanol, propyl alcohol, isopropyl alcohol or butyl alcohol; hydrocarbon type solvents such as hexane, heptane, octane, isooctane, decane or liquid paraffin; ether type solvents such as dimethyl ether, diethyl ether or tetrahydrofuran; ketone type solvents such as acetone or methyl ethyl ketone; ester type solvents such as methyl acetate, ethyl acetate or butyl acetate; and chloride type solvents such as methylene chloride, chloroform or carbon tetrachloride, dimethylformamide, diethylformarmide, dimethylsulfoxide, dioxane or the like can be used. These solvents may be used by mixing two or more of them. It is preferable to select a solvent having a higher boiling point than the starting temperature of the polymerization initiator used.

The polymerization initiator is not limited in particular as long as it has the ability to start radical polymerization. For example, in addition to peroxides such as benzoyl peroxide and azo compounds such as azobisisobutyronitrile or dimethyl 2,2'-azobis(isobutyrate), persulfuric acid type polymerization initiators such as potassium persulfate or ammonium persulfate can be used. Also, the polymerization may be obtained with a photochemical reaction or a radioactive emission without depending on polymerization initiators.

The polymerization temperature is higher than the starting temperature of each polymerization initiator. For example, in a case of a peroxide type polymerization initiator, the polymerization temperature may be about 70° C.

Although the polymerization time is not restricted in particular, it is usually 2 to 24 hours. It is desirable to react about 1 day when it is expected to obtain a polymer having relative high molecular weight. When the reaction time is too short, unreacted monomer will be left and molecular weight will become relative low.

The average molecular weight of the copolymer in accordance with the present invention is not restricted, and it can exhibit the expected effect as long as the copolymer has a higher polymerization degree than that of an oligomer. However, as will be mentioned later, the cross-linking reaction rate will become slow when the polymerization degree is low. Also, applicability or workability will be inferior since viscosity becomes higher when the polymerization degree is too large. Accordingly, the average molecular weight of the copolymer is preferably about 2,000 to 150,000.

The copolymer of the present invention comprises the functional silyl groups in its molecule. Therefore, molecules of the copolymer are cross-linked by hydrolyzing, thereby forming the cross-linked copolymer. When such a cross-linking reaction is conducted on the material to be treated, a coating of the cross-linked copolymer is formed on the surface to which it is applied.

The forming reaction of such cross-linked coating will be considered as follows. FIG. 1 typically shows the reaction comprising Monomer (A) as a constituent monomer. The trifunctional silyl group —$SiR_3R_4R_5$, of Monomer (A) is readily hydrolyzed with water, acid, alkali or the like, thereby turning into a trihydroxysilyl group —$Si(OH)_3$. This trihydroxysilyl group forms a stable siloxane bond Si—O—Si by reacting with another trihydroxysilyl group. As a result, the cross-linked copolymer is formed wherein molecules of the copolymer are cross-linked in the form of three-dimensional network.

Accordingly, when the copolymer is hydrolyzed on the material to be treated, cross-linking occurs on its applied portion, the cross-linked copolymer forms a strong network state coating on the surface of the material to be treated. When the cross-linked copolymer synthesized in advance before it is applied on the material to be treated, it becomes a gel or plastic. Therefore, the cross-linked copolymer synthesized in advance is very difficult to apply.

A method for forming the cross-linked coating with the copolymer of the present invention is characterized in that a composition of the present invention is hydrolyzed on the material to be treated to cross-link molecules of the copolymer. In the present invention, human hair or human epidermis such as skin, nails, eyelashes, eyebrows or the like are preferable as the material to be treated. Also, materials such as fiber, paper or glass can be treated.

As a method for cross-linking, a reaction with water, acid, or alkali or a reaction with heat can be used. Specifically, after applying the composition of the present invention on the material to be treated, the composition is hydrolyzed to cross-link by bringing the applied portion into contact with water (water vapor or the like may be accepted), acid or alkali or by heating the applied portion. Also, hydrolysis and cross-linking may be conducted by applying the composition on the material treated with water, acid or alkali in advance. Also, the method of applying immediately after water, acid or alkali is mixed with the composition of the present invention may be considered. Generally, however, it is preferable to apply the composition and water, acid, alkali or the like separately. When the composition of the present invention is used as a cosmetic pack, the method of applying immediately after water, acid or alkali is mixed with the composition of the present invention is preferable in terms of strippability. The reaction with water, acid or alkali may be effected while heating. However, it is also sufficient to treat at room temperature. Also, it is possible to cross-link naturally with moisture in the atmosphere without bringing the applied portion into contact with acid, water or alkali, when the cross-linking reaction may move slowly. In any case, instruments such as a brush, a comb, a hair brush or a spray can be used as the occasion demands so as to uniformly apply and treat the composition.

The acid and alkali used in the coating-forming method of the present invention are not limited in particular, as long as they can cross-link the copolymers by hydrolysis. An organic or inorganic acid and alkali can be used. One or more of these acids and alkalis may be used, and also the mixture thereof with water may be used.

The composition in accordance with the present invention comprises the above-mentioned copolymer as an indispensable ingredient. A preferable embodiment of the composition can be a non-aqueous composition containing said copolymer.

The non-aqueous composition can be, for example, a composition wherein the copolymer is dissolved or dispersed in an organic solvent. Examples of the organic solvent include aliphatic hydrocarbons, aromatic hydrocarbons, chlorine compound type hydrocarbons, ether type solvents, alcohol type solvents, aliphatic mono- to tetra-valent alcohols having 1 to 4 carbon atoms, cellosolve type solvents such as ethylcellosolve or butylcellosolve, dioxane, methyl acetate or diformamide. Among these solvents, aliphatic mono- to di-valent alcohols are preferable as cosmetic ingredients. Examples thereof include methanol, ethanol, isopropanol and propylene glycol. In particular, ethanol or isopropanol is preferable in terms of safety.

When the composition of the present invention is a moisture containing composition, it is preferable to prepare the composition just before applying because the cross-linking reaction occurs in the product. Such moisture containing composition also belongs to the category of the present invention.

A preparation form of the composition in accordance with the present invention is not limited, and any form can be used as long as the effect of the present invention can be exhibited. For example, it can be a liquid lotion, milky lotion, cream, gel, mist, spray, aerosol, mousse and the like.

The other ingredients can be mixed into the composition of the present invention within a range that the effect of the present invention is not spoiled. For example, ingredients mixed in cosmetics are normally surfactants, humectants, ultraviolet protectors, pH adjustors, antiseptics, antioxidants, chelating agents, thickening agents, film-forming ingredients, oily components, polymers or propellants. It is preferable that water, acid or alkali is mixed in an another composition excluding the copolymer. However, it is possible to mix water, acid or alkali into the composition containing the copolymer of the present invention, as long as they are applied to the material to be treated immediately after its preparation.

When the other film-forming ingredients are mixed into the composition along with the copolymer of the present invention, a preferable film-forming ingredient can be the siliconized polysaccharide shown by Formula (XI):

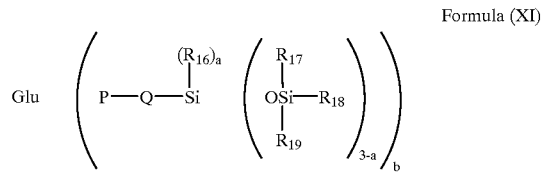

Formula (XI)

wherein Glu is a sugar residue of a polysaccharide; P is a divalent group for bonding; Q is a divalent aliphatic group; $R_{16}$ is a monovalent organic group having 1–8 carbon atoms; and $R_{17}$, $R_{18}$, and $R_{19}$ each is a monovalent organic group having 1–8 carbon atoms or a siloxy group shown by —$OSiR_{20}R_{21}R_{22}$, wherein $R_{20}$, $R_{21}$ and $R_{22}$ each is a monovalent organic group having 1–8 carbon atoms; and a is 0, 1 or 2, and b is an integer of positive number.

In Formula (XI), Glu is a sugar residue of a polysaccharide. Various known polysaccharides can be used. For example, in addition to cellulose, hemicellulose, gum arabic, tragacanth gum, tamarind gum, pecfin, starch, mannan, guar gum, locust bean gum, quince seed gum, alginic acid, carrageenan, agar, xanthan gum, dextran, pullulan, chitin, chitosan, hyaluronic acid and chondroitin sulfate, a derivative of these polysaccharides such as polysaccharide derivatives that are made by carboxymethylation, sulfation, phosphorylation, methylation, ethylation, addition of an alkylene oxide such as ethylene oxide or propylene oxide, acylation, cationization, or lowering of molecular weight can be used. Among them, ethylcellulose or pullulan is preferable and pullulan is more preferable. In the present invention, though an average molecular weight of the polysaccharide differs according to the land of the polysaccharide, in general about 1,000 to 5,000,000 is preferable.

These polysaccharides have at least one of reactive functional group such as a hydroxyl or carboxyl group according to the kind. The divalent group for bonding shown by P is a group derived from A, which is formed by reacting the reactive functional group of the polysaccharide with a silicone compound shown by the following Formula (XII):

Formula (XII)

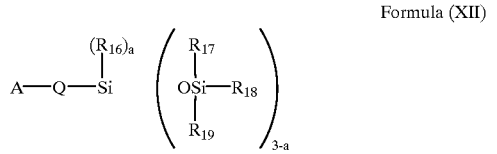

wherein Q, $R_6$, $R_7$, $R_8$, $R_9$ and a are the same as defined in Formula (XI), and A is a functional group that can react with a reactive functional group of a polysaccharide. For example, isocyanate, epoxy, vinyl, acryloyl, methacryloyl, amino, imino, hydroxyl, carboxyl, mercapto group or the like can be used as A.

In the reaction between such a silicone compound and polysaccharide, known methods such as the method described in Japanese Unexamined Patent Publication No. 8-134103, can be used.

Examples of P include carbamoyl group, —CH2CH(OH)—, carbonyl group, amino group and ether group. Among them, a carbamoyl group —CONH—, which is formed by reaction of the compound of Formula (XII) wherein A is isocyanate group (O=C=N—) with a hydroxyl group of the polysaccharide, is preferable. The sugar residue of the polysaccharide in this case represents the rest of the polysaccharide excluding the hydrogen atom of the hydroxyl group reacting with the isocyanate group. Similarly, the sugar residue of a polysaccharide is defined when P is other than carbamoyl group.

As for the divalent aliphatic group shown by Q, an alkylene group, an alkylene group comprising oxygen atom, nitrogen atom, sulfur atom or the like in main chain, an alkylene group comprising an arylene group such as phenylene group in main chain, and an alkylene group comprising carbonyloxy group or oxycarbonyl group in main chain can be used. These divalent aliphatic groups can have a substituent such as hydroxy, alkoxy, alkyl group or the like, and the terminal atom of the aliphatic group may be a hetero atom such as oxygen atom, nitrogen atom or sulfur atom. Q can be —(CH2)2—, —(CH2)3—, —(CH2)4—, —(CH2)6—, —(CH2)8—, —{CH2CH(CH3)}—, —(CH2)2O(CH2)3—, —CH2CH(OH)—CH2— or the like. Propylene group shown by —(CH2)3— is preferable.

In Formula (XI), the monovalent organic group having 1–8 carbon atoms shown in $R_{16}$, $R_{17}$, $R_{18}$, $R_{19}$, $R_{20}$, $R_{21}$ and $R_{22}$, can be an alkyl group such as methyl, ethyl, propyl or butyl group; a cycloalkyl group such as cyclopentyl or cyclohexyl group; an aryl group such as phenyl group; an aralkyl group such as benzyl group; an alkenyl group such as vinyl or allyl group, an fluorinated alkyl group such as 3,3,3-trifluoropropyl group; or the like can be listed. An alkyl group is preferable as such an organic group. Methyl group is more preferable.

Also, each of $R_{17}$, $R_{18}$ and $R_{19}$ may be a siloxy group shown by —OSiR20R21R22. Examples of the siloxy group include a trimethylsiloxy, ethyldimethylsiloxy, phenyldimethylsiloxy, vinyldimethylsiloxy and 3,3,3-trifluoropropyldimethylsiloxy group. Also, $R_{16}$, $R_{17}$, $R_{18}$, $R_{19}$, $R_{20}$, $R_{21}$ and $R_{22}$ may be the same or different each other. In the siliconized polysaccharide of the present invention, it is preferable that a=0 and $R_{17}$, $R_{18}$ and $R_{19}$ each is methyl group.

In the present invention, a more preferable siliconized polysaccharide may be a siliconized pullulan shown by the following Formula (XIII):

Formula (XIII)

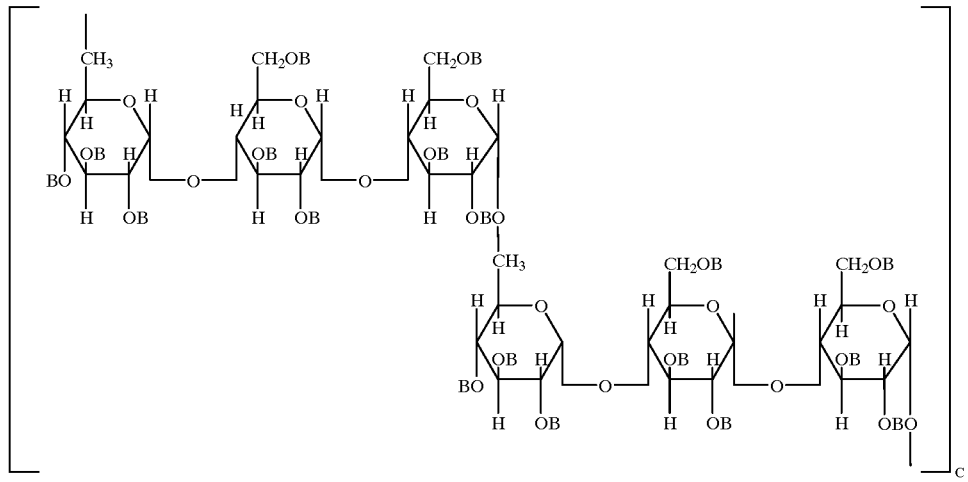

wherein B is a hydrogen atom or a group shown by —CONH(CH2)3Si[OSi(CH3)3] and its substitution degree is 0.5–2.5; and c is a number from 100 to 20,000.

In the present invention, the substitution degree of the siliconized polysaccharide represents an average number of the silicone compound bonding to one unit of constituent sugar of the polysaceharide. For example, the substitution degree of the above-mentioned siliconized pullulan is the average number of the substituent —CONH(CH2)3Si[OSi (CH)] bonding to the base unit of pullulan shown by the following Formula (XIV):

Formula (XIV)

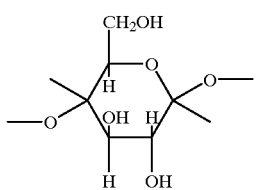

Hair-nature modifying effect, damaged hair recovering effect, resistance to shampooing, color retention effect or the like can be improved by using the copolymer containing reactive silyl groups together with the siliconized polysaccharide. Further, flaking when the composition is repeatedly applied can be inhibited.

When the siliconized polysaccharide which is dissolved in a solvent such as a silicone oil having low molecular weight or light isoparaffin is used, facility for compounding and feeling of use at the application time can be ameliorated. As for the silicone oil having low molecular weight, linear dimethyl polysiloxane having 2–7 carbon atoms or cyclic dimethyl polysiloxane having 3–7 carbon atoms is preferable. Although an amount of the siliconized polysaccharide in the composition is not restricted in particular, it is 0.01 to 20 wt % in general and, preferably, 0.2 to 10 wt %.

In the following, the effect of the composition in accordance with the present invention will be described in detail. Structures of each monomer used in the following are shown below. Also, the compounding amount is wt % unless otherwise stated.

Monomer A1:

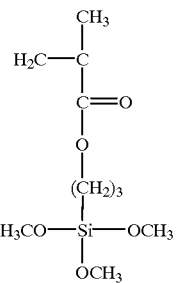

Monomer A2:

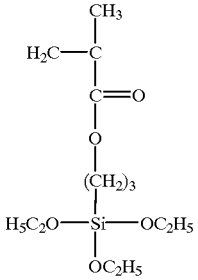

Monomer B1:

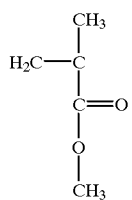

Monomer C1 (molecular weight 422) and Monomer C2 (molecular weight 12,000):

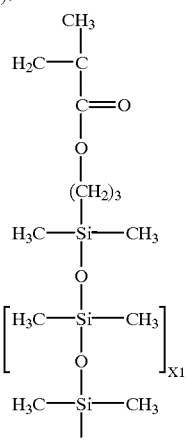

Monomer C3 (molecular weight 5,000):

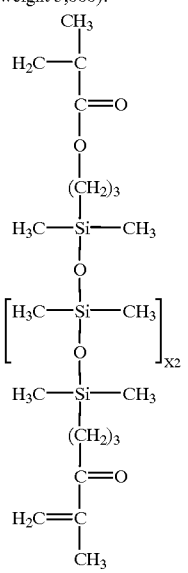

Monomer C4:

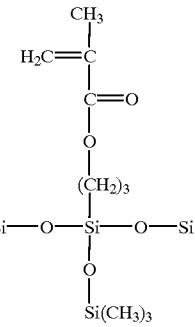

Monomer D1:

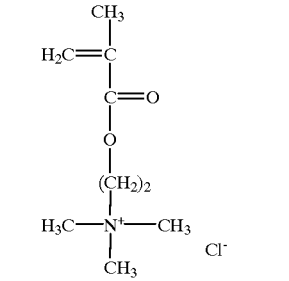

<Cosmetics for Hair Coating>

Many people are not satisfied with their hair. For example, the people who have soft hair desire to give tension and hardness to their hair. Many hair treatment preparations and hair styling preparations have been developed.

However, any such conventional hair treatment or hair styling preparations are only temporary. Because swimming, bathing or shampooing wash them off, the effect is lost. Accordingly, as the nature of hair can not be fundamentally improved even when such preparations are used, it is necessary to use such hair cosmetic preparations daily. Further, there are very few hair cosmetic preparations that can exhibit satisfactory effect.

Also, irrespective of age or sex, people color their hair according to their own taste. This accounts for the use of temporary hair colorants such as colorant spray and semi-permanent hair colorant such as acidic hair colorant. These can easily color hair without damaging it.

However, because a temporary or semipermanent hair colorant is easily washed off by shampooing or the like, better color retention is desired.

Therefore, the effect when the composition comprising a copolymer of the present invention was treated on hair, was studied.

Test Example 1-1 i) Synthesis of Copolymer

Copolymer 1-1

2.0 g (8 mmol) of 3-methacryloxypropyltrimethoxysilane (Monomer A1) and 8.0 g (80 mmol) of methyl methacrylate (Monomer B1) were dissolved in 100 ml of ethanol and the mixture was heated while stirring under a nitrogen gas stream for 1 hour at 70° C. 0.05 g of potassium persulfate was added to the solution and the mixture was reacted over night. The reaction mixture was cooled to room temperature and concentrated under a vacuum. The residue was dissolved in 10 ml of ethanol and the solution was added to 500 ml of n-hexane. The deposits were collected to obtain the copolymer.

In the NMR spectral data (solvent CDCl3 or DMSO-d6) of the resulting copolymer, a signal of hydrogen atom in $CH_2=C$ of a monomer used as a starting material was not observed at or near 6–7 ppm. As a result, generation of copolymer was confirmed. Also, in the present invention, generation of the copolymers was confirmed in a similar manner.

Copolymer 1-2

In a similar manner to Copolymer 1-1, except for using 4.0 g (16 mmol) of 3-methacryloxypropyltrimethoxysilane and 8.0 g (80 mmol) of methyl methacrylate, the copolymer was obtained.

Copolymer 1-3

In a similar manner to Copolymer 1-1, except for using 8.0 g (32 mmol) of 3-methacryloxypropyltrimethoxysilane and 4.0 g (40 mmol) of methyl methacrylate, the copolymer was obtained.

Copolymer 1-4

In a similar manner to Copolymer 1-1, except for using 10.0 g (40 mmol) of 3-methacryloxypropyltrimethoxysilane and 2.0 g (20 mmol) of methyl methacrylate, the copolymer was obtained.

Copolymer 1-5

In a similar manner to Copolymer 1-1, except for using 10.0 g (40 mmol) of 3-methacryloxypropyltrimethoxysilane and 0.4 g (4 mmol) of methyl methacrylate, the copolymer was obtained.

Copolymer 1-6

In a similar manner to Copolymer 1-1, except for using 10.0 g (40 mmol) of 3-methacryloxypropyltrimethoxysilane, the copolymer was obtained.

ii) Test Method

Each of the Copolymers 1-1 to 1-6 was tested by the following method 3 parts by weight of each copolymer was dissolved in 97 parts by weight of ethanol and the solution which was filled into a spray container was used as a sample.

(Hair-nature modifying effect)

20 professional panelists were used for evaluating their feelings. Approximately 2 g of the spray solution was sprayed on the hair of each panelist and the hair was washed with a commercially available shampoo. The tension and hardness after natural drying of the hair were evaluated by the following standard by means of questionnaires.

⊚: Among 20 panelists, 16 or more answered their hair had tension and hardness.

○: Among 20 panelists, 12 to 15 answered their hair had tension and hardness.

Δ: Among 20 panelists, 6 to 11 answered their hair had tension and hardness.

X: Among 20 panelists, 0 to 5 answered their hair had tension and hardness.

(Resistance to shampooing)

After studying the hair-nature modifying effect, washing the hair with shampoo and drying each was repeated in 3 cycles. The hair tension and hardness were evaluated with an evaluation standard which depended on the feelings of the panelists as follows.

⊚: Among 20 panelists, 16 or more answered that the effect was maintained and resistance to shampooing was exhibited.

○: Among 20 panelists, 12 to 15 answered that the effect was maintained and resistance to shampooing was exhibited.

Δ: Among 20 panelists, 6 to 11 answered that the effect was maintained and resistance to shampooing was exhibited.

X: Among 20 panelists, 0 to 5 answered that the effect was maintained and resistance to shampooing was exhibited.

(Flaking)

In the hair-nature modifying effect test mentioned above, the presence of flaking was judged by visual inspection. The evaluation standard was as follows.

⊚: Flaking was not observed absolutely.

Δ: Flaking was observed slightly.

X: Flaking was observed clearly.

TABLE 1

| Copolymer | Monomer (wt %) A1/B1 | Hair-nature modifying effect | Resistance to shampooing | Flaking |
|---|---|---|---|---|
| 1-1 | 20/80 | ⊚ | Δ | ⊚ |
| 1-2 | 33/67 | ⊚ | ○ | ⊚ |
| 1-3 | 67/33 | ⊚ | ⊚ | ⊚ |
| 1-4 | 83/17 | ⊚ | ⊚ | ⊚ |
| 1-5 | 96/4 | ○ | ○ | Δ |
| 1-6 | 100/0 | Δ | Δ | Δ |

From TABLE 1, it is shown that a coating of the cross-linked copolymer containing Monomer A as a constituent monomer possesses a hair-nature modifying effect.

The resistance to shampooing was not sufficient and continuity of the hair-nature modifying effect was inferior when Monomer (A) was low in the copolymer. On the other hand, both the hair-nature modifying effect and the resistance to shampooing tended to be lower and flaking was easily generated when Monomer (A) was 100%. Therefore, as for the monomer composition of the copolymer, Monomer (A) in the copolymer is 25 to 99 wt % and preferably is 40 to 85 wt %.

Test Example 1-2

The spray prepared in Test Example 1-1 was used as a sample and color retention was tested by the following method.

(Color retention)

A commercially available acidic hair colorant was uniformly applied on white human hair. 3 minutes later, the hair was washed with water and dried naturally. 5 g of the colored hair(control) was taken and approximately 1 g of the spray sample was sprayed thereon. Hair washing with commercially available shampoo and natural drying were repeated ten times with respect to the hair with or without treatment of the spray. The color of the shampoo-treated hair was compared to the control that was not treated with shampoo by observing with naked eyes and evaluated as follows.

⊚: Absolutely no discoloring occurred.
○: Almost no discoloring occurred.
Δ: Discoloring occurred.
X: Discoloring occurred remarkably.

TABLE 2

| Copolymer | Monomer (wt %) A1/B1 | Color retention |
|---|---|---|
| 1-1 | 20/80 | Δ |
| 1-2 | 33/67 | ○ |
| 1-3 | 67/33 | ⊚ |
| 1-4 | 83/17 | ⊚ |
| 1-5 | 96/4 | ○ |
| 1-6 | 100/0 | Δ |
| Nothing (not sprayed) | — | x |

As shown in TABLE 2, discoloring caused by shampooing was remarkably observed when the hair was not treated with the copolymer. On the contrary, when the hair was treated with the copolymer, discoloring was inhibited and color retention was improved. Therefore, a coating of the cross-linked copolymer of the present invention can improve the color retention when the copolymer was treated on the colored hair. This improving effect is remarkably exhibited when the percentage of Monomer (A) in the copolymer is 25 to 99 wt % and, preferably, 40 to 85 wt %.

Test Example 1-3

Next, the copolymers which have the monomer composition of TABLE 3 were synthesized in the same way as Test Example 1-1 and tested similar to Test Examples 1-1 and 1-2. Also, smoothness and texture were evaluated according to the following method.

(Smoothness)

Smoothness of the hair after hair-nature modifying effect test was evaluated by means of questionnaires according to the following standard.

⊚: Among 20 panelists, 16 or more answered that the hair felt smooth.
○: Among 20 panelists, 12 to 15 answered that the hair felt smooth.
Δ: Among 20 panelists, 6 to 11 answered that the hair felt smooth.
X: Among 20 panelists, 0 to 5 answered that the hair felt smooth.

(Texture)

Texture of the hair after hair-nature modifying effect test was evaluated by means of questionnaires according to the following standard.

⊚: Among 20 panelists, 15 or more answered favorably.
○: Among 20 panelists, 10 to 14 answered favorably.
Δ: Among 20 panelists, 5 to 9 answered favorably.
X: Among 20 panelists, 0 to 5 answered favorably.

TABLE 3

| Copolymer | Monomer (wt %) A1 | B1 | C* | Hair-nature modifying effect | Resistance to shampooing | Flaking | Color retention | Smoothness |
|---|---|---|---|---|---|---|---|---|
| 1-7 | 33 | 67 | — | ⊚ | ○ | ⊚ | ○ | Δ |
| 1-8 | 67 | 33 | — | ⊚ | ⊚ | ⊚ | ⊚ | Δ |
| 1-9 | 50 | 10 | 40(C1) | ⊚ | ⊚ | ⊚ | ⊚ | ⊚ |
| 1-10 | 50 | 10 | 40(C2) | ⊚ | ⊚ | ⊚ | ⊚ | ⊚ |
| 1-11 | 50 | 40 | 10(C3) | ⊚ | ⊚ | ⊚ | ⊚ | ⊚ |
| 1-12 | 60 | 35 | 5(C4) | ⊚ | ⊚ | ⊚ | ⊚ | ⊚ |
| 1-13 | 50 | — | 50(C2) | Δ | ⊚ | ⊚ | ⊚ | ⊚ |
| 1-14 | 25 | — | 75(C4) | Δ | ○ | ⊚ | ○ | ⊚ |

*The inside of ( ) represents Monomer (C) used.

As is shown in TABLE 3, the hair-nature modifying effect, the resistance to shampooing and the color retention are improved and smoothness of hair after treatment can be remarkably improved by introducing Monomer (C) into the copolymer consisting of Monomers (A) and (B). Also, although the hair-nature modifying effect was low and the copolymer was difficult to treat due to stickiness in the copolymers 1-13 and 1-14, these copolymers had good properties in terms of the resistance to shampooing, the color retention effect and smoothness.

As shown in the foregoing, the percentage of Monomer (C) in the copolymer is 1 wt % or more and, preferably, 5 wt % or more. It was also indicated that Monomer (B) in the copolymer contributed to the hair-nature modifying effect and the prevention of stickiness of the copolymer. The percentage of Monomer (B) in the copolymer was 1 wt % or more and, preferably, 10 wt % or more.

TABLE 4

| Co-polymer | Monomer (wt %) | | | | Hair-nature modifying effect | Resistance to shampooing | Color retention | Texture |
|---|---|---|---|---|---|---|---|---|
| | A2 | B1 | C4 | D1 | | | | |
| 1-12 | 60 | 35 | 5 | — | ◎ | ◎ | ◎ | △ |
| 1-15 | 60 | 35 | 5 | 10 | ◎ | ◎ | ◎ | ◎ |
| 1-16 | 60 | 35 | 5 | 20 | ◎ | ○ | ○ | ◎ |
| 1-17 | 60 | 35 | 5 | 50 | ○ | ○ | ○ | ◎ |
| 1-18 | 60 | 35 | 5 | 100 | △ | × | × | ◎ |

As shown in TABLE 4, the copolymer consisted of Monomers (A) to (D) can give smoothness, good texture and moist feeling to hair. When the percentage of Monomer (D) was high, the hair-nature modifying effect, the resistance to shampooing and the color retention tended to be lower because the hydrophilic nature of the cross-linked coating increases. Accordingly, the percentage of Monomer (D) is 1 to 100 wt % and, more preferably, 5 to 50 wt % with respect to the entire amount of Monomers (A) to (C) in the copolymer.

As mentioned above, by effecting a cross-linking reaction after applying the composition comprising the copolymer having reactive silyl groups on hair, tension and hardness are given to the hair. At the same time, because an excellent resistance to shampooing is obtained, the effect is maintained without loss even after repeating shampooing. Also, the hair treated with the copolymer has smoothness and texture without stiffness and flaking does not occur. Further, when this treatment was effected on colored hair, discoloring by shampooing is inhibited and color retention is remarkably improved.

It is suggested that these effects are exhibited because a cross-linking reaction occurs on the hair by hydrolyzing the copolymer and the cross-linked coating forms. The coating strongly coats the hair in a network state and gives excellent resistance to washing.

Accordingly, the composition of the present invention is useful as a cosmetic for hair coating or for modifying the nature of hair.

A preferable example of the copolymer to be used in the cosmetic for hair coating or for modifying the nature of hair in accordance with the present invention can be shown by Formulas (VIII), (IX) or (X).

As a monomer composition of the copolymer, the percentage of Monomer (A) in the copolymer is 25 to 99 wt % and, more preferably, 40 to 85 wt %. When Monomer (A) is too low, the resistance to shampooing is low and the hair-nature modifying effect and the color retention effect may not be sufficiently maintained since the amount available for cross-linking is low. On the contrary, the hair-nature modifying effect, the color retention and the resistance to shampooing tend to be lower when Monomer (A) is too high. Also, flaking occurs easily. Here the cross-linking reaction does not progress neatly and a large amount of the unreacted part remains in the copolymer because the part for cross-linking is too high.

Monomer (B) adjusts the ratio of Monomer (A) and contributes to hair-nature modifying effect and water-repellency of the coating of the cross-linked copolymer. Monomer (B) also inhibits flaking. The percentage of Monomer (B) is 1 wt % or more and, more preferably, 10 wt % or more of the copolymer. The percentages of the other monomers decrease and the copolymer has poor solubility against alcohol type solvents when Monomer (B) is too high. Therefore, the percentage of Monomer (B) is 75 wt % or less and, preferably, 60 wt % or less.

Monomer (C) has a siloxane part to improve the water-repellency and the resistance to shampooing of the cross-linked coating and to give the hair after treatment smoothness. Monomer (C) can also inhibit flaking. The percentage of Monomer (C) is 1 wt % or more and, preferably, 5 wt % or more in the copolymer of the present invention.

However, when the percentage of Monomer (C) is too high, the percentages of the other monomers become relatively small and the resistance to shampooing tends to be poor. Therefore, the percentage of Monomer (C) is 70 wt % or less and, preferably, 60 wt % or less.

Also, when the copolymer comprising Monomer (D) as a constituent monomer is applied to the hair, good texture can be given to the hair and moist feeling of use can be obtained. However, when the percentage of Monomer (D) is too high, the water-repellency, the resistance to shampooing and the like become poor because the hydrophilic nature of the coating becomes high due to the amine portion contained in Monomer (D). The percentage of Monomer (D) is 1 to 100 wt % and, preferably, 5 to 50 wt % with respect to the combined amount of Monomers (A) to (C).

Although a concentration of the copolymer is not restricted in particular, it is preferably 0.1 to 10 wt % and, more preferably, 1 to 5 wt %. When an amount of the copolymer is too low, the preferred effect can not be obtained with one treatment. On the contrary, when the amount of the copolymer is too high, applicability, spreadability, smoothness, texture and the like become inferior and flaking may occur.

The effect when the copolymer of the present invention and the other film-forming ingredients were used together was studied. As for the film-forming ingredient, siliconized pullulan (substitution degree is 1.7, molecular weight of pullulan used as a staring material is approximately 200,000), which is one of the siliconized polysaccharides was used.

Test Example 1-4

A sample was prepared according to the prescription of TABLE 5 and tested by the following method.

(Hair-nature modifying effect)

20 professional panelists evaluated according to their feelings. After approximately 2 g of the sample was sprayed on the hair of each panelist, the hair was washed with water. The tension and the hardness of the hair after natural drying were evaluated by means of questionnaires according to the following standard (just after the test). Also, the tension and the hardness of the hair after repeatedly washing with a commercially available shampoo and natural drying 5 times were also evaluated according to the following standard.

⊚: 16 or more answered that their hair had tension and hardness.

○: 12 to 15 answered that their hair had tension and hardness.

Δ: 6 to 11 answered that their hair had tension and hardness.

X: 0 to 5 answered that their hair had tension and hardness.

(Damaged hair recovering effect)

20 professional panelists who had damaged hair were evaluated for their feelings. Approximately 2 g of the sample was sprayed on the hair of each panelist and then the hair was washed with water. The touch(smoothness) after natural drying was evaluated by means of questionnaires according to the following standard (just after the test). Also, the touch after repeatedly washing with a commercially available shampoo and natural drying 5 times was also evaluated according to the following standard.

⊚: 16 or more answered that the touch was smooth and a damaged hair recovering effect was obtained.

○: 12 to 15 answered that the touch was smooth and a damaged hair recovering effect was obtained.

Δ: 6 to 11 answered that the touch was smooth and a damaged hair recovering effect was obtained.

X: 0 to 5 answered that the touch was smooth and a damaged hair recovering effect was obtained.

(Color retention)

The color retention was tested according to the method of Test Example 1-2.

(Flaking on repeated applications)

After approximately 2 g of the sample was sprayed on the hair of 20 professional panelists, and then the hair was washed with water and dried naturally. The presence of flaking after the above-mentioned cycle was repeated 3 times was judged by visual inspection. The evaluation standard is as follows.

⊚: Flaking was not observed at all.

Δ: Flaking was observed slightly.

X: Flaking was observed clearly.

TABLE 5

| Ingredient* | Amount | | | | | | | | | | |
|---|---|---|---|---|---|---|---|---|---|---|---|
| Copolymer 1-19 | 5 | — | — | — | — | — | 5 | — | — | — | — |
| Copolymer 1-20 | — | 5 | — | — | — | — | — | 5 | — | — | — |
| Copolymer 1-21 | — | — | 5 | — | — | — | — | — | 5 | — | — |
| Copolymer 1-22 | — | — | — | 5 | — | — | — | — | — | 5 | — |
| Copolymer 1-23 | — | — | — | — | 5 | — | — | — | — | — | 5 |
| Siliconized pullulan | — | — | — | — | — | 5 | 0.5 | 0.5 | 0.5 | 0.5 | 0.5 |
| Ethanol | 35 | 35 | 35 | 35 | 35 | 40 | 35 | 35 | 35 | 35 | 35 |
| Light isoparaffin | 60 | 60 | 60 | 60 | 60 | 55 | 59.5 | 59.5 | 59.5 | 59.5 | 59.5 |
| Hair-nature modifying effect | | | | | | | | | | | |
| Just after test | ⊚ | ⊚ | ⊚ | ⊚ | Δ | Δ | ⊚ | ⊚ | ⊚ | ⊚ | ○ |
| After 5 times shampooing | ○ | ⊚ | ⊚ | ⊚ | Δ | Δ | ⊚ | ⊚ | ⊚ | ⊚ | ○ |
| Damaged hair recovering effect | | | | | | | | | | | |
| Just after test | ○ | ○ | ○ | Δ | ○ | ⊚ | ⊚ | ⊚ | ⊚ | ⊚ | ⊚ |
| After 5 times shampooing | Δ | ○ | ○ | Δ | ○ | ⊚ | ⊚ | ⊚ | ⊚ | ⊚ | ⊚ |
| Color retention | ○ | ⊚ | ⊚ | ⊚ | ⊚ | Δ | ⊚ | ⊚ | ⊚ | ⊚ | ⊚ |
| Flaking on repeated applications | Δ | Δ | Δ | x | Δ | ⊚ | ⊚ | ⊚ | ⊚ | ⊚ | ⊚ |

*The monomers (wt %) of each copolymer are as follows.
Copolymer 1-19: A2-B1-C3-D1 = 60-35-5-20
Copolymer 1-20: A2-B1-C1 = 50-40-10
Copolymer 1-21: A2-B1-C2 = 50-25-25
Copolymer 1-22: A2-B1 = 67-33
Copolymer 1-23: A2-B1 = 50-50

As shown in TABLE 5, when the copolymer and siliconized pullulan were used together, the hair-nature modifying effect and the color retention effect can be equal to or can be improved as compared to the case where the copolymer only is used. Also, the touch was smoother as compared to the case where the copolymer only was used and the damaged hair recovering effect was remarkable. Also, these effects were maintained even after repeating shampooing. Further, though flaking on repeated applications of the copolymer may be occur when the copolymer only was used, it can be inhibited by using siliconized pullulan together.

TABLE 6

| Ingredient | Amount | | | | | | | |
|---|---|---|---|---|---|---|---|---|
| Copolymer 1-19 | 5 | 5 | 5 | 2 | 2 | 1 | 0.1 | — |
| Siliconized pullulan | — | 0.1 | 0.5 | 0.5 | 2 | 5 | 5 | 5 |
| Ethanol | 35 | 35 | 35 | 38 | 39 | 39 | 39.9 | 40 |
| Light isoparaffin | 60 | 59.9 | 59.5 | 59.5 | 59 | 55 | 55 | 55 |
| Hair-nature modifying effect | | | | | | | | |
| Just after test | ⊚ | ⊚ | ⊚ | ⊚ | ⊚ | ⊚ | ○ | Δ |
| After 5 times shampooing | ○ | ⊚ | ⊚ | ⊚ | ⊚ | ○ | Δ | Δ |
| Damaged hair recovering effect | | | | | | | | |
| Just after test | ○ | ○ | ⊚ | ⊚ | ⊚ | ⊚ | ⊚ | ⊚ |
| After 5 times shampooing | Δ | ○ | ⊚ | ⊚ | ⊚ | ⊚ | ⊚ | ⊚ |
| Color retention | ○ | ⊚ | ⊚ | ⊚ | ⊚ | ○ | Δ | x |
| Flaking on repeated applications | Δ | ⊚ | ⊚ | ⊚ | ⊚ | ⊚ | ⊚ | ⊚ |

TABLE 6 is the result of the test which was conducted as in Test Example 1-1 with changing the ratios of the copolymer and siliconized pullulan. The hair-nature modifying effect and the color retention tends to be lower when the copolymer is low. On the other hand, the hair-nature modifying effect, the color retention and the damaged hair recovering effect were not sufficiently improved and flaking on repeated applications may occur when siliconized pullulan is low. Accordingly, the ratio between the copolymer and siliconized pullulan by weight is preferably 100: 1 and, more preferably, 50:1–1:1.

As described above, by using a copolymer containing reactive silyl groups together with a siliconized polysaccharide, a composition where the hair-nature modifying effect, the color retention and the damaged hair recovering effect are high and maintained when shampooing is repeated. Also, flaking on repeated applications of the copolymer can be inhibited.

When only the siliconized polysaccharide is used, the hair-nature modifying effect and the color retention effect are low as compared to the case where only the copolymer was used. Therefore, it is shown that these effects are improved by using the siliconized polysaccharide together with the copolymer. This is because the siliconized polysaccharide is included into the cross-linked coating, thereby, at the time of forming the cross-linked coating, the cross-linked coating and the siliconized polysaccharide act synergistically.

Examples 1-1 to 1-3 Hair Spray

The test has been conducted in the same manner as Test Examples 1-1 and 1-2 by using the hair sprays of TABLE 7. Every example was superior to Comparative Example 1-1 in the hair-nature modifying effect, the resistance to shampooing, the flaking and the color retention.

TABLE 7

| Ingredient | Example 1-1 | Example 1-2 | Example 1-3 | Comp. Ex. 1-1 |
|---|---|---|---|---|
| (1) Copolymer 1-1 | 1 | 3 | 5 | — |
| (2) Polyvinylpyrrolidone/ vinyl acetate copolymer | — | — | — | 5 |
| (3) Ethanol | 47 | 45 | 43 | 43 |
| (4) POE (40) hydrogenated castor oil | 1 | 1 | 1 | 1 |
| (5) Octyl palmitate | 1 | 1 | 1 | 1 |
| (6) LPG (3.5kg/cm² at 20° C.) | 50 | 50 | 50 | 50 |
| (7) Perfume | q.s. | q.s. | q.s. | q.s. |
| Hair-nature modifying effect | ○ | ◉ | ◉ | ○ |
| Resistance to shampooing | Δ | Δ | Δ | x |
| Flaking | ◉ | ◉ | ◉ | x |
| Color retention | Δ | Δ | Δ | x |

(Manufacturing process)

The ingredient (1) or (2) was dissolved in the ingredient (3) and the ingredients (4), (5) and (7) were added to the solution. The mixture was filled into an aerosol container and then the ingredient (6) was added thereto, thereby obtaining a hair spray.

Examples 1-4 to 1-6 Hair Mist Applicator

The test has been conducted in the same manner as Test Examples 1-1 and 1-2 by using the hair sprays of TABLE 8. Every example was superior to Comparative Example 1-2 in the hair-nature modifying effect, the resistance to shampooing, the flaking and the color retention.

TABLE 8

| Ingredient | Example 1-4 | Example 1-5 | Example 1-6 | Comp. Ex. 1-2 |
|---|---|---|---|---|
| (1) Copolymer 1-2 | 1 | 3 | 5 | — |
| (2) Polyvinylalcohol/ vinyl acetate copolymer | — | — | — | 5 |
| (3) Ethanol | 97 | 95 | 93 | 93 |
| (4) POE (9) lauryl ether | 1 | 1 | 1 | 1 |
| (5) Dimethylpolysiloxane (5 cps) | 1 | 1 | 1 | 1 |
| (6) Perfume | q.s. | q.s. | q.s. | q.s. |
| Hair-nature modifying effect | ◉ | ◉ | ◉ | ○ |
| Resistance to shampooing | ○ | ○ | ○ | x |
| Flaking | ◉ | ◉ | ◉ | x |
| Color retention | ○ | ○ | ○ | x |

(Manufacturing process)

The ingredient (1) or (2) was dissolved in the ingredient (3). The ingredients (4) to (6) were added to the solution and then the mixture was filled into a container, thereby obtaining a hair mist applicator.

Examples 1-7 to 1-9 Hair Spray

The test has been conducted in the same manner as Test Examples 1-1 and 1-2 by using the hair sprays of TABLE 9. Every example was superior to Comparative Example 1-3 in the hair-nature modifying effect, the resistance to shampooing, the flaking and the color retention.

TABLE 9

| Ingredient | Example 1-7 | Example 1-8 | Example 1-9 | Comp. Ex. 1-3 |
|---|---|---|---|---|
| (1) Copolymer 1-4 | 1 | 3 | 5 | — |
| (2) Polyvinylpyrrolidone/ vinyl acetate copolymer | — | — | — | 5 |
| (3) Ethanol | 54.5 | 52.5 | 50.5 | 50.5 |
| (4) POE (100) hydrogenated castor oil | 1 | 1 | 1 | 1 |
| (5) Highly-polymerized dimethylpolysiloxane (500 cps) | 0.5 | 0.5 | 0.5 | 0.5 |
| (6) Dimethylpolysiloxane (5 cps) | 3 | 3 | 3 | 3 |
| (7) LPG (3.5 kg/cm² at 20° C.) | 40 | 40 | 40 | 40 |
| (8) Perfume | q.s. | q.s. | q.s. | q.s. |
| Hair-nature modifying effect | ○ | ◉ | ◉ | Δ |
| Resistance to shampooing | ◉ | ◉ | ◉ | x |
| Flaking | ◉ | ◉ | ◉ | Δ |
| Color retention | ◉ | ◉ | ◉ | x |

(Manufacturing process)

The ingredient (1) or (2) was dissolved in the ingredient (3) and the ingredients (4), (5) and (7) were added to the solution. The mixture was filled into an aerosol container and the ingredient (6) were added thereto, thereby obtaining a hair spray.

Examples 1-10 to 1-12 Hair Spray

The test has been conducted in the same manner as Test Examples 1-1 and 1-2 by using the hair sprays of TABLE 10. Every example was superior to Comparative Example 1-4 in the hair-nature modifying effect, the resistance to shampooing, the flaking, the color retention and smoothness.

TABLE 10

| Ingredient | Example 1-10 | Example 1-11 | Example 1-12 | Comp. Ex. 1-4 |
|---|---|---|---|---|
| (1) Copolymer 1-9 | 1 | — | — | — |
| (2) Copolymer 1-11 | — | 1 | — | — |
| (3) Copolymer 1-14 | — | — | 1 | — |
| (4) Polyvinylpyrrolidone/vinyl acetate copolymer | — | — | — | 1 |
| (5) Ethanol | 47.0 | 47.0 | 47.0 | 47.0 |
| (6) POE (40) hydrogenated castor oil | 1 | 1 | 1 | 1 |
| (7) Octyl palmitate | 1 | 1 | 1 | 1 |
| (8) LPG | 50 | 50 | 50 | 50 |
| (9) Perfume | q.s. | q.s. | q.s. | q.s. |
| Hair-nature modifying effect | ⊚ | ⊚ | ⊚ | ○ |
| Resistance to shampooing | ⊚ | ⊚ | ⊚ | x |
| Flaking | ⊚ | ⊚ | ⊚ | x |
| Color retention | ○ | ⊚ | ⊚ | x |
| Smoothness | ⊚ | ⊚ | ⊚ | x |

(Manufacturing process)

The ingredients (1) to (4) were dissolved in the ingredient (5) and the ingredients (6), (7) and (9) were added to the solution. The mixture was filled into an aerosol container and the ingredient (8) was added thereto, thereby obtaining a hair spray.

Examples 1-13 to 1-15 Hair Mist Applicator

The test has been conducted in the same manner as Test Examples 1-1 and 1-2 by using the hair mist applicators of TABLE 11. Every example was superior to Comparative Example 1-5 in the hair-nature modifying effect, the resistance to shampooing, the flaking, the color retention and smoothness.

TABLE 11

| Ingredient | Example 1-13 | Example 1-14 | Example 1-15 | Comp. Ex. 1-5 |
|---|---|---|---|---|
| (1) Copolymer 1-8 | 1 | — | — | — |
| (2) Copolymer 1-10 | — | 1 | — | — |
| (3) Copolymer 1-11 | — | — | 1 | — |
| (4) Polyvinylalcohol/vinyl acetate copolymer | — | — | — | 1 |
| (5) Ethanol | 97.0 | 97.0 | 97.0 | 97.0 |
| (6) POE (9) hydrogenated castor oil | 1 | 1 | 1 | 1 |
| (7) Dimethylpolysiloxane | 1 | 1 | 1 | 1 |
| (8) Perfume | q.s. | q.s. | q.s. | q.s. |
| Hair-nature modifying effect | ⊚ | ⊚ | ⊚ | ○ |
| Resistance to shampooing | ⊚ | ⊚ | ⊚ | x |
| Flaking | ⊚ | ⊚ | ⊚ | x |
| Color retention | ○ | ⊚ | ⊚ | x |
| Smoothness | ⊚ | ⊚ | ⊚ | x |

(Manufacturing process)

The ingredients (1) to (4) were dissolved in the ingredient (5) and the ingredients (6) to (8) were added to the solution. A hair mist applicator was obtained by filling the mixture into a container.

Example 1-16

The copolymers 1-24 to 1-26 were synthesized by the following method and tested in the same manner as Test Examples 1-1 and 1-2. As a result, every copolymer had the high hair-nature modifying effect, the resistance to shampooing and the color retention, and was favorable in feeling of use as shown in TABLE 12. Also, flaking was not observed in every case.

Copolymer 1-24

12.0g of Monomer A2 and 6.0 g of monomer B1 were dissolved in 100 ml of ethanol and the solution was heated while stirring under a nitrogen gas stream for 1 hour at 70° C. 0.05 g of dimethyl 2,2'-azobis(isobutyrate) was added to the solution and the mixture was reacted over night. The reaction mixture was cooled to room temperature and was concentrated under a vacuum. The residue was dissolved in 10 ml of ethanol and the solution was added to 500 ml of n-hexane. The deposit was collected, thereby obtaining the copolymer.

Copolymer 1-25

In a similar manner to Copolymer 1-24, except for using 10.0 g of Monomer A2, 2.0 g of Monomer B1, and 1.0 g of Monomer D1, the copolymer was obtained.

Copolymer 1-26

In a similar manner to Copolymer 1-24, except for using 10.0 g of Monomer A2, 10.0 g of Monomer C4, and 0.5 g of Monomer D1, the copolymer was obtained.

TABLE 12

| Copolymer | Monomer (wt %) A2 | B1 | C4 | D1 | Hair-nature modifying effect | Resistance to shampooing | Coloring retention | Smoothness | Texture |
|---|---|---|---|---|---|---|---|---|---|
| 1-24 | 67 | — | — | 33 | ⊚ | ○ | ○ | ○ | ⊚ |
| 1-25 | 77 | 15 | — | 8 | ⊚ | ⊚ | ⊚ | ○ | ⊚ |
| 1-26 | 49 | — | 49 | 2 | ⊚ | ⊚ | ⊚ | ⊚ | ⊚ |

Example 1-17 Hair Spray

| | |
|---|---|
| (1) Copolymer 1-22 | 5 wt % |
| (2) Siliconized pullulan | 1 |
| (3) Dimethylpolysiloxane (5 mPa.s) | 5 |
| (4) Ethanol | 15 |
| (5) Light isoparaffin | 34 |
| (6) LPG (3.5 kg/cm$^2$ at 20° C.) | 40 |
| (7) Perfume | q.s. |

(Manufacturing Process)

Siliconized pullulan was dissolved in light isoparaffin. The ethanol solution of dimethylpolysiloxane, perfume and Copolymer were added thereto. The mixture was filled into an aerosol container and LPG added thereto, thereby obtaining a hair spray.

This hair spray improved the hair-nature modifying effect, the damaged hair recovering effect and the resistance to shampooing, and inhibited flaking on repeated applications as compared to the hair spray without siliconized pullulan compounded thereto.

| Example 1-18 Hair Mist Applicator | |
|---|---|
| (1) Copolymer 1–20 | 3 wt % |
| (2) Siliconized pullulan | 0.1 |
| (3) Stearyltrimethylammonium chloride | 0.5 |
| (4) Ethanol | 37 |
| (5) Light isoparaffin | 49.4 |
| (6) Dimethylpolysiloxane (5 mPa.s) | 10 |
| (7) Perfume | q.s. |

(Manufacturing Process)

Siliconized pullulan was dissolved in light isoparaffin. The ethanol solution of dimethylpolysiloxane, perfume, copolymer and stearyltrimethylammonium chloride were added thereto. A hair mist applicator was obtained by filling the mixture into a spray container.

This hair mist applicator improved the hair-nature modifying effect, the damaged hair recovering effect and the resistance to shampooing and inhibited flaking on repeated applications as compared to the hair mist applicator without siliconized pullulan compounded thereto.

| Example 1-19 Hair Coating | |
|---|---|
| (1) Copolymer 1–19 | 3 wt % |
| (2) Siliconized pullulan | 0.5 |
| (3) Stearyltrimethylammonium chloride | 0.5 |
| (4) Ethanol | 37 |
| (5) Light isoparaffin | 19 |
| (6) LPG (3.5 kg/cm$^2$ at 20° C.) | 40 |
| (7) Perfume | q.s. |

(Manufacturing Process)

Siliconized pullulan was dissolved in light isoparaffin. The ethanol solution of dimethylpolysiloxane, perfume, copolymer and stearyltrimethylammonium chloride were added thereto. The mixture was filled into an aerosol container and LPG was added thereto, thereby obtaining a hair coating.

This hair coating could improve the color retention of hair that was colored with temporary or acidic hair colorant, as compared to the hair coating without siliconized pullulan compounded thereto.

<Cosmetics for Skin Coating>

Many people suffer from rough skin, nail cracking or dermatopathy caused by water or detergent. In particular, beauticians, people engaged in medical work, a housewives or the like have a serious problem with nail cracking and rough skin and are ready to pass into a chronic state due to repeated cleaning and washing. Also, the people who have a delicate sldn have a problem that barber's itch or the like which easily occurs in shaving.

In order to protect nails or skin from such external irritations, there is a method for coating them.

Also, for improving the make-up cosmetic retention, there is a method for coating on the body portion where the make-up cosmetics are applied thereon. For example, a top coating of nail enamel and a coating cosmetic preparation which is used for putting on mascara or eyebrow make-up are known well.

However, cosmetic coating preparations having sufficient effects such as water-repellency, resistance to washing, make-up retention or the like have not been obtained.

Accordingly, the case where the compositions comprising the copolymer containing reactive silyl groups are treated on a portion excluding hair such as skin or nails was studied to determine the effect.

| Test Example 2-1 Skin-Protecting Effect Prescription 2-1: | |
|---|---|
| Glyceryl tri-2-ethylhexanoate | 1.0 wt % |
| 1,3-Butyleneglycol | 1.0 |
| Ethanol | 96.0 |
| Copolymer | 2.0 |
| Vitamin A acetate | q.s. |

A sample solution was prepared by the above-described prescription 2-1. As a control, a solution using ethanol instead of the copolymer was also prepared in the same way. Each preparation was filled into a spray container and the skin-protecting effect thereof was tested.

(Skin-Protecting Effect)

The sample was sprayed on the portion to be shaved in 20 male panelists. After washing the treated portion with water, moisture was wiped with a towel. Then, a beard was shaved with a razor and the condition of skin roughness after shaving was evaluated The evaluation standard is as follows.

⊚: Among 20 panelists, 16 or more evaluated that skin roughness was very low.

○: Among 20 panelists, 12 to 15 evaluated that skin roughness was very low.

Δ: Among 20 panelists, 6 to 11 evaluated that skin roughness was very low.

X: Among 20 panelists, 0 to 5 evaluated that skin roughness was very low.

TABLE 13

| Copolymer | Monomer (wt %) A1/B1 | Skin-Protecting Effect |
|---|---|---|
| 2-1 | 20/80 | Δ |
| 2-2 | 33/67 | ○ |
| 2-3 | 67/33 | ⊚ |
| 2-4 | 83/17 | ⊚ |
| 2-5 | 96/4 | ○ |
| 2-6 | 100/0 | Δ |
| Nothing (Ethanol) | — | x |

As shown in TABLE 13, the cross-linked coating formed by the copolymer containing Monomer (A) as a constituent monomer had skin-protecting effect.

Also, the skin-protecting effect tended to be lower when Monomer (A) in the copolymer was too low or too high. Accordingly, it was shown that the percentage of Monomer (A) was preferably 25 to 99 wt % and, more preferably, 40 to 85 wt %.

Test Example 2-2

A sample solution was prepared by dissolving 3 parts by weight of a copolymer into 97 parts by weight of ethanol and the nail enamel retention thereof was tested Namely, nails of both hands of female panelists were coated with a red nail enamel, which was commercially available. After drying, only the right hand nails were coated with the sample solution using a nail enamel brush. After drying, the both hands were washed with water and moisture was wiped with a towel. After 1 week, the state of the right hand nails were evaluated by using the left hand nails as a control. Flaking was also evaluated. The evaluation standard was as follows.

(Evaluation standard of enamel retention)

⊚: Peeling of nail enamel was not observed at all.

◯: Peeling of nail enamel was observed hardly.

Δ: Peeling of nail enamel was observed.

X: Peeling of nail enamel was observed remarkably.

(Evaluation standard of flaking)

⊚: Flaking was not observed at all.

Δ: Flaking was observed slightly.

X: Flaking was observed clearly.

TABLE 14

| Copoly-mer | Monomer (wt %) A1/B1 | Enamel Retention Right hand | Control (left hand) | Flaking Right hand |
|---|---|---|---|---|
| 2-1 | 20/80 | Δ | x | ⊚ |
| 2-2 | 33/67 | ◯ | x | ⊚ |
| 2-3 | 67/33 | ⊚ | x | ⊚ |
| 2-4 | 83/17 | ⊚ | x | ⊚ |
| 2-5 | 96/4 | ◯ | x | Δ |
| 2-6 | 100/0 | Δ | x | Δ |

As shown in TABLE 14, peeling of nail enamel was observed remarkably and the color of nails was off when the copolymer was not applied. On the contrary, peeling of nail enamel was inhibited and the color retention was improved when the copolymer was applied over the nail enamel.

Also, this effect tended to be lower when Monomer (A) in the copolymer was too low or too high. Accordingly, the percentage of Monomer (A) in the copolymer was preferably 25 to 99 wt % and, more preferably, 40 to 85 wt %.

Test Example 2-3

Next, the copolymer having the monomer composition of TABLE 15 was tested in the same way as Test Examples 2-1 and 2-2. Also, feeling of use in skin-protecting effect test was evaluated according to the following standard.

(Evaluation standard of feeling of use)

⊚: Among 20 panelist, 16 or more answered that feeling of use was good.

◯: Among 20 panelists, 12 to 15 answered that feeling of use was good.

Δ: Among 20 panelists, 6 to 11 answered that feeling of use was good.

X: Among 20 panelists, 0 to 5 answered that feeling of use was good.

TABLE 15

| Copolymer | Monomer (wt %) | | | Skin-Protecting Effect | Feeling of Use |
|---|---|---|---|---|---|
| | A2 | B1 | C* | | |
| 2-7 | 33 | 67 | — | ◯ | ◯ |
| 2-8 | 50 | 10 | 40(C1) | ⊚ | ⊚ |
| 2-9 | 50 | 10 | 40(C2) | ⊚ | ⊚ |
| 2-10 | 50 | 40 | 10(C3) | ⊚ | ⊚ |
| 2-11 | 60 | 35 | 5(C4) | ⊚ | ⊚ |
| 2-12 | 35 | 55 | 10(C2) | ⊚ | ⊚ |
| 2-13 | 50 | — | 50(C2) | ⊚ | ⊚ |
| 2-14 | 25 | — | 75(C4) | ◯ | ⊚ |

*The inside of ( ) represents Monomer (C.) used.

TABLE 16

| Copoly-mer | Monomer (wt %) | | | Enamel Retention | | Feeling of Use |
|---|---|---|---|---|---|---|
| | A2 | B1 | C* | Right hand | Left hand (control) | |
| 2-7 | 33 | 67 | — | ◯ | x | ⊚ |
| 2-8 | 50 | 10 | 40(C1) | ⊚ | x | ⊚ |
| 2-9 | 50 | 10 | 40(C2) | ⊚ | x | ⊚ |
| 2-10 | 50 | 40 | 10(C3) | ⊚ | x | ⊚ |
| 2-11 | 60 | 35 | 5(C4) | ⊚ | x | ⊚ |
| 2-12 | 35 | 55 | 10(C2) | ⊚ | x | ⊚ |
| 2-13 | 50 | — | 50(C2) | ⊚ | x | ⊚ |
| 2-14 | 25 | — | 75(C4) | ◯ | x | ⊚ |

*The inside of ( ) represents Monomer (C.) used.

As shown in TABLE 15 and 16, feeling of use could be improved along with the skin-protecting effect and the enamel retention by introducing Monomer (C). Also, Monomer (C) contributed to inhibition of flaking. Although copolymers 2-13 and 2-14 which consisted of Monomers (A) and (C) were difficult to use due to stickiness, the skin-protecting effect, the enamel retention and the feeling of use were fully satisfied.

Consequently, the percentage of Monomer (C) in the copolymer was preferably 1 wt % or more and, more preferably, 5 wt % or more. Also, Monomer (B) in the copolymer contributed to prevention of stickiness of the copolymer. Accordingly, it was indicated that the percentage of Monomer (B) was preferably 1 wt % or more and, more preferably, 10 wt % or more.

As mentioned above, when nails, skin, eyebrows, eyelashes or the like are coated with the copolymer containing reactive silyl groups and the cross-linking reaction is effected, the coated portion is protected by a coating. The coating has excellent water-repellency and resistance to washing and has no adhesion against the object to be contacted. Also, such protecting effect can be exhibited continuously, since the coating does not come off easily, even when water or detergent is used for washing. Further, feeling of use is not stiffened and no flaking occurs.

For example, barber's itch can be prevented when the skin cosmetics of the present invention are used as a preshaving lotion before shaving. Also, when the skin cosmetics of the present invention are applied over a make-up cosmetic such as nail enamel, the retention of the make-up cosmetic is considerably improved.

When crosslinking occurs on the coated portion, the copolymer forms a cross-linked coating which is excellent in the water-repellency and the resistance to washing and the coated portion is strongly coated with the coating in a network state. Accordingly, the coated portion is uniformly protected.

Therefore, the composition of the present invention is useful as a cosmetic for skin coating. The cosmetic for skin coating of the present invention can be applied on eyebrows, eyelashes or the like, in addition to skin and nails.

Preferred examples of the copolymer for the cosmetic for skin coating of the present invention can include the copolymers shown by Formulas (VIII) and (IX).

As a monomer composition of the copolymer, the percentage of Monomer (A) in the copolymer is preferably 25 to 99 wt % and, more preferably, 40 to 85 wt %. When the percentage of Monomer (A) is too low, the water-repellency and the resistance to washing is low and effects such as skin-protecting effect or improving effect of make-up retention may not be sufficiently exhibited, since the part for the cross-linking reaction is low. On the other hand, when the percentage of Monomer (A) is 100 wt %, the skin-protecting effect and improving effect of make-up retention tends to be lower. Also, flaking occurs easily. Here the cross-linking reaction does not progressed neatly and a large amount of the unreacted part remains on the copolymer because the cross-linking reaction part is too high.

Monomer (B) adjusts the ratio of Monomer (A). Also, Monomer (B) contributes to the water-repellency and inhibits flaking. The percentage of Monomer (B) in the copolymer is 1 wt % or more and, preferably, 10 wt % or more. When Monomer (B) is too high, the percentages of other monomers are lowered and the copolymer tends to have poor solubility against alcohol type solvents. Therefore, the percentage of Monomer (B) is 75 wt % or less and, preferably, 60 wt % or less.

Monomer (C) has a siloxane part. Accordingly, Monomer (C) can improve the water-repellency and the resistance to washing of the cross-linked coating and make feeling of use favorable. Also, Monomer (C) can inhibit flaking. The percentage of Monomer (C) is 1 wt % or more and, preferably, 5 wt % or more in the copolymer of the present invention. However, when the percentage of Monomer (C) is too high, the percentages of the other monomers become relatively low and the resistance to washing tends to be poor. Therefore, the percentage of Monomer (C) is 70 wt % or less and, preferably, 60 wt % or less.

Also, when the copolymer, which comprises Monomer (D) as a constituent monomer along with the above-mentioned Monomers (A) to (C), is used, the percentage of Monomer (D) in the copolymer is 100 wt % or less and, preferably, 50 wt % or less with respect to the combined amount of Monomers (A) to (C). When the percentage of Monomer (D) is too high, the water-repellence, the resistance to washing and the like become poor because the hydrophilic nature of the coating becomes high due to the amine portion contained in Monomer (D).

Although the amount of the copolymer in the cosmetic for skin coating in accordance with the present invention is not restricted, it is preferably 0.1 to 10 wt % and, more preferably, 1 to 5 wt %. When the amount is too low, a sufficient effect can not be obtained with one treatment. On the contrary, applicability, spreadability and the like may become poor and flaking may occur when the amount is too high.

As for the cosmetic for skin coating in accordance with the present invention, in addition to a hand lotion and a preshaving lotion, there can be a top coating for nail enamel and a coating cosmetic over mascara or eyebrow make-up.

Also, the above-mentioned siliconized polysaccharide can be used in the cosmetic for skin coating of the present invention.

| Example 2-1 Mascara Coating | |
|---|---|
| Polyacrylate emulsion | 30 wt % |
| Solid paraffrin | 8 |
| Light isoparaffrin | 10 |
| Sorbitan sesquioleate | 4 |
| Ethanol | 46 |
| Copolymer 2-4 | 2 |
| Antiseptic | q.s. |
| Perfume | q.s. |

(Manufacturing Process)

Each ingredient was mixed at 70° C., successively. The mixture was unified with a homomixer to obtain a mascara coating.

When this mascara coating was applied with a brush after applying a commercially-available mascara and dried naturally, the retention of the mascara was improved.

| Example 2-2 Nail Coating | |
|---|---|
| Nitrocellulose | 10 wt % |
| Epoxy-denatured phthalic alkyd resin | 5 |
| Sucrose benzoate | 5 |
| Acetyltriethyl citrate | 5 |
| Ethyl acetate | 20 |
| Butyl acetate | 20 |
| Ethanol | 30 |
| Copolymer 2-5 | 5 |

(Manufacturing Process)

Each ingredient was mixed and the mixture was shaken for 1 hour at room temperature to obtain a nail coating.

When this nail coating was applied with a brush after applying a commercially-available nail enamel and dried naturally, the retention of the nail enamel was improved.

| Example 2-3 Mascara Coating | |
|---|---|
| Polyacrylate emulsion | 30 wt % |
| Solid paraffin | 8 |
| Light isoparaffm | 10 |
| Sorbitan sesquioleate | 4 |
| Ethanol | 46 |
| Copolymer 2-8 | 2 |
| Antiseptic | q.s. |
| Perfume | q.s. |

(Manufacturing Process)

Each ingredient was mixed at 70° C., successively and the mixture was unified with a homomixer to obtain a mascara coating.

When this mascara coating was applied with a brush after applying a commercially-available mascara and dried naturally, the retention of the mascara was improved and the feeling of use thereof was very smooth favorably.

| Example 24 Nail Coating | |
|---|---|
| Nitrocellulose | 10 wt % |
| Epoxy-denatured phthalic alkyd resin | 5 |
| Sucrose benzoate | 5 |
| Acetyltriethyl citrate | 5 |
| Ethyl acetate | 20 |

-continued

| Example 24 Nail Coating | |
| --- | --- |
| Butyl acetate | 20 |
| Ethanol | 30 |
| Copolymer 2-11 | 5 |

(Manufacturing Process)

Each ingredient was mixed and the mixture was shaken for 1 hour at room temperature to obtain a nail coating, When this nail coating was applied with a brush after applying a commercially-available nail enamel and dried naturally, the retention of the nail enamel was improved. Also, the feeling of use thereof was very smooth favorably.

<Cosmetics Containing Pigment and/or Acidic Dye>

A pigment or dye is used for various cosmetics as a coloring material.

Hair colorants are classified broadly into: (1) a temporary hair colorant which uses a pigment as a main coloring ingredient and which adheres the coloring ingredient only on the surface of the hair (e.g., coloring stick, colorant spray or the like); (2) a semipermanent hair colorant (acidic hair colorant) which uses an acidic dye as a main coloring ingredient and which penetrates a part of the coloring ingredient into the inside of the hair; and (3) a permanent hair colorant (oxidation hair colorant) which uses an oxidation dye as a main coloring ingredient and which colors deep into the hair.

Among these hair colorants, although the oxidation hair colorant can maintain its color, it has problems such as hair easily damaged, eruption or coloring of the scalp, and difficulty of use.

Although the temporary and semipermanent hair colorants do not cause hair damage or skin irritation and can be used conveniently, there are disadvantages that color retention is poor and the hair colorants come off easily. Accordingly, it is desired to improve the color retention of such temporary or semipermanent hair colorant.

In addition to such hair cosmetics, a pigment or dye is an essential ingredient in make-up cosmetics. It is also desired to improve the water-repellency and the make-up retention in such make-up cosmetics.

Therefore, the effect when the copolymer containing reactive silyl groups was used with the cosmetic containing a pigment or acidic dye was studied.

| Test Example 3-1 i) Preparation of Sample Prescription 3-1: | |
| --- | --- |
| (1) Copolymer | 2 or 3 wt % |
| (2) Carbon black | 2 |
| (3) Ethanol | 44.8 or 43.8 |
| (4) Beeswax | 10 |
| (5) Japanese wax | 10 |
| (6) Castor oil | 30 |
| (7) POE (20) sesquioleate | 1.2 |
| (8) Perfume | q.s. |
| (9) Antioxidant | q.s. |

(Manufacturing Process)

Oily ingredients and carbon black were added into an ethanol solution of the copolymer, successively. After adding perfume and antioxidant into the mixture, a temporary hair colorant was obtained by stirring sufficiently.

ii) Test Method

Each sample was applied on white hair and the hair was left for 3 minutes. Then the hair was washed with water and dried naturally. The presence of flaking was evaluated at this time. Thereafter, the hair was washed with a commercially available shampoo and dried naturally, to evaluate color retention by visual inspection. Also, a hair colorant, which contained ethanol instead of the copolymer, was prepared as a control and tested in the same manner. The evaluation standard is as follows.

(Evaluation standard for color retention)

⊚: Coloring effect was maintained for 7 days or more.

◯: Coloring effect was maintained for 4–6 days.

Δ: Coloring effect was maintained for 2–3 days.

X: No durability.

(Evaluation standard for flaking)

⊚: Flaking was not observed at all.

Δ: A Flaking was observed slightly.

X: Flaking was observed clearly.

TABLE 17

| | Monomer (wt %) | Color Retention | | Flaking |
| --- | --- | --- | --- | --- |
| Copolymer | A1/B1 | 2 wt % | 3 wt % | 3 wt % |
| 3-1 | 20/80 | Δ | ◯ | ⊚ |
| 3-2 | 33/67 | ◯ | ⊚ | ⊚ |
| 3-3 | 67/33 | ◯ | ⊚ | ⊚ |
| 3-4 | 83/17 | ◯ | ⊚ | ⊚ |
| 3-5 | 96/4 | ◯ | ⊚ | ⊚ |
| 3-6 | 100/0 | Δ | ◯ | Δ |
| Nothing (Ethanol) | — | X | X | ⊚ |

As shown in TABLE 17, the temporary hair colorant which uses the copolymer is excellent in the resistance to washing and is considerably improved in color retention as compared to the case that the copolymer is not used.

Test Example 3-2

A liquid acidic hair colorant was prepared according to the following prescription 3-2. The color retention and the flaking were tested in the same way as the above Test Example 3-1.

| Prescription 3-2: | |
| --- | --- |
| Copolymer | 2 or 3 wt % |
| Acidic dye (Natrozole) | 1 |
| Ethanol | 20.7 or 19.7 |
| Benzyl alcohol | 6 |
| Isopropyl alcohol | 20 |
| Lactic acid | 0.3 |
| Silicone KF-56 | 50 |
| (manufactured by Shin-Etsu Chemical Co., Ltd.) | |
| Perfume | q.s. |
| Antioxidant | q.s. |

TABLE 18

| | Monomer (wt %) | Color Retention | | Flaking |
| --- | --- | --- | --- | --- |
| Copolymer | A1/B1 | 2 wt % | 3 wt % | 3 wt % |
| 3-1 | 20/80 | Δ | ◯ | ⊚ |
| 3-2 | 33/67 | ◯ | ⊚ | ⊚ |
| 3-3 | 67/33 | ◯ | ⊚ | ⊚ |
| 3-4 | 83/17 | ◯ | ⊚ | ⊚ |
| 3-5 | 96/4 | ◯ | ⊚ | ⊚ |

TABLE 18-continued

| Copolymer | Monomer (wt %) A1/B1 | Color Retention 2 wt % | 3 wt % | Flaking 3 wt % |
|---|---|---|---|---|
| 3-6 | 100/0 | Δ | ○ | Δ |
| Nothing (Ethanol) | — | Δ | Δ | ⊚ |

As shown in TABLE 18, an excellent resistance to washing is exhibited and the color retention is improved even when the copolymer of the present invention is used in an acidic hair colorant Also, when the percentage of Monomer (A) in the copolymer is too low or too high, the resistance to washing becomes poor and the color retention tends to be lower. Accordingly, the percentage of Monomer (A) in the copolymer is preferably 25 to 99 wt % and, more preferably, 40 to 85 wt %.

Test Example 3-3

Next, by using the copolymer having a monomer composition of TABLE 21, a temporary and acidic hair colorants were prepared according to the following prescriptions 3-1 and 3-2, respectively. These hair colorants were tested in the same way as Test Example 3-1. A compounding amount of each copolymer was 2 wt %. Also, in the color retention test, smoothness and texture after applying the sample, washing with water and natural drying were evaluated according to the evaluation standard of the above Test Example 1-3.

TABLE 19

Temporary hair colorant (prescription 3-1, copolymer 2 wt %)

| Copolymer | Monomer (wt %) A2 | B1 | C* | Color Retention | Smoothness | Flaking |
|---|---|---|---|---|---|---|
| 3-7 | 67 | 33 | — | ○ | ○ | ⊚ |
| 3-8 | 50 | 10 | 40(C1) | ⊚ | ⊚ | ⊚ |
| 3-9 | 50 | 10 | 40(C2) | ⊚ | ⊚ | ⊚ |
| 3-10 | 50 | 40 | 10(C3) | ⊚ | ⊚ | ⊚ |
| 3-11 | 60 | 35 | 5(C4) | ⊚ | ⊚ | ⊚ |
| 3-12 | 50 | — | 50(C2) | ○ | ⊚ | ⊚ |
| 3-13 | 25 | — | 75(C4) | Δ | ⊚ | ⊚ |

TABLE 20

Acidic hair colorant (prescription 3-2, copolymer 2 wt %)

| Copolymer | Monomer (wt %) A2 | B1 | C* | Color Retention | Smoothness | Flaking |
|---|---|---|---|---|---|---|
| 3-7 | 67 | 33 | — | ○ | ○ | ⊚ |
| 3-8 | 50 | 10 | 40(C1) | ⊚ | ⊚ | ⊚ |
| 3-9 | 50 | 10 | 40(C2) | ⊚ | ⊚ | ⊚ |
| 3-10 | 50 | 40 | 10(C3) | ⊚ | ⊚ | ⊚ |
| 3-11 | 60 | 35 | 5(C4) | ⊚ | ⊚ | ⊚ |
| 3-12 | 50 | — | 50(C2) | ⊚ | ⊚ | ⊚ |
| 3-13 | 25 | — | 75(C4) | ○ | ⊚ | ⊚ |

*The inside of ( ) represents Monomer (C) used.

As shown in TABLES 19 and 20, along with the color retention of the hair colorant, the feeling of use of the hair after treatment is improved by introducing Monomer (C) into the copolymer. Although copolymers 3-12 and 3-13 which consisted of Monomers (A) and (C) were difficult to use due to stickiness, the color retention and smoothness were fully satisfied.

Consequently, the percentage of Monomer (C) in the composition is preferably 1 wt % or more and, more preferably, 5 wt % or more. Also, Monomer (B) in the copolymer contributed to prevention of stickiness of the copolymer. Accordingly, it is shown that the percentage of Monomer (D) is preferably 1 wt % or more and, more preferably, 10 wt % or more.

TABLE 21

Temporary hair colorant (prescription 3-1, copolymer 2 wt %)

| Copolymer | Monomer (wt %) A2 | B1 | C4 | D1 | Color Retention | Texture |
|---|---|---|---|---|---|---|
| 3-11 | 60 | 35 | 5 | — | ⊚ | Δ |
| 3-14 | 60 | 35 | 5 | 10 | ⊚ | ⊚ |
| 3-15 | 60 | 35 | 5 | 20 | ○ | ⊚ |
| 3-16 | 60 | 35 | 5 | 50 | ○ | ⊚ |
| 3-17 | 60 | 35 | 5 | 100 | X | ⊚ |

As shown in TABLE 21, good texture and moist touch of the hair can be obtained when the copolymer consists of Monomers (A) to (D). Also, when a percentage of Monomer (D) is higher, the color retention tends to be lower because the hydrophilic nature of the cross-inked coating becomes high. This tendency was the same for the acidic hair colorants. Accordingly, the percentage of Monomer (D) is 1 to 100 wt % and, preferably, 5 to 50 wt % with respect to the combined amount of Monomers (A) to (C) in the composition.

Where the cosmetics using the copolymer containing reactive silyl groups along with a coloring material such as pigment or acidic dye are applied on the hair, and then the cross-linking reaction is effected, thus applied cosmetics exhibit an excellent water-repellency and resistance to washing and have no adhesion against contacted objects. Also, the color retention of the hair is remarkably improved. Further, the feeling of use is not stiffened and no flaking occurs. Even when the cosmetic of the present invention is applied as a make-up cosmetic, the same effects can be exhibited and make-up retention is considerably improved.

Such effects can be understood as follows. A cross-linked coating strongly coats the applied portion in a network state which envelopes the coloring material such as pigment or acidic dye. Accordingly, a coating which is excellent in the water-repellency and the resistance to washing can be formed.

Therefore, the composition using the copolymer containing reactive silyl groups and a pigment and/or an acidic dye is useful as a cosmetic and, in particular, as a hair colorant. The composition is useful as a temporary or acidic hair colorant and a make up cosmetic.

Preferred examples of the copolymer used in such cosmetics can include the copolymers shown by Formulas (VIII), (IX) or (X).

As a monomer composition of the copolymer, the percentage of Monomer (A) in the copolymer is preferably 25 to 99 wt % and, more preferably, 40 to 85 wt %. When the percentage of Monomer (A) is too low, the water-repellency and the resistance to washing may be low and the make-up retention may not be sufficiently improved, since the part for the cross-linking reaction is low. On the other hand, the water-repellency, the resistance to washing and the make-up retention tend to be lower even when the percentage of Monomer (A) is 100 wt %. Also, flaking occurs easily. It is believed that the cross-linking reaction is not progressed neatly and a large amount of the unreacted part remains on the copolymer because the cross-linking reaction part is too high.

Monomer (B) adjusts the ratio of Monomer (A). Also, it contributes to the water-repellency and inhibits flaking. The percentage of Monomer (B) is 1 wt % or more and, preferably 10 wt % or more in the copolymer. When Monomer (B) is too high, the percentages of other monomers are decreased and the copolymer begins to have poor solubility against alcohol type solvents. Therefore, the percentage of Monomer (B) in the copolymer is 75 wt % or less and, preferably, 60 wt % or less.

Monomer (C) has a siloxane part. Monomer (C) can improve the water-repellency and the resistance to washing of the cross-linked coating and make the feeling of use smooth and favorable. Also, Monomer (C) can inhibit flaking. The percentage of Monomer (C) is 1 wt % or more and, preferably, 5 wt % or more in the copolymer of the present invention. However, when the percentage of Monomer (C) is too high, the percentages of the other monomers become relatively low and the resistance to washing tends to be poor. Therefore, the percentage of Monomer (C) in the copolymer is 70 wt % or less and, preferably, 60 wt % or less.

Also, when the copolymer containing Monomer (D) as a constituent monomer is used to treat hair, good texture and a moist feeling of use can be obtained. However, when the percentage of Monomer (D) is too high, the water-repellency, the resistance to washing and the like become poor because the hydrophilic nature of the coating becomes high due to the amine portion contained in Monomer (D). The percentage of Monomer (D) is 1 to 100 wt % and, preferably, 5 to 50 wt % with respect to the combined amount of Monomers (A) to (C).

Although a compounding amount of the copolymer is not restricted, it is preferably 0.1 to 10 wt % and, more preferably, 1 to 5 wt %. When the compounding amount is too low, a sufficient effect can not be obtained with one treatment. On the contrary, applicability, spreadability and the like become poor and flaking may occur when the compounding amount is too high.

The pigment and acidic dye, which are used in the cosmetic of the present invention are not restricted as long as these are generally compounded into cosmetics.

As for the acidic dye, in specific, any legal color which is noticed in "Ministerial Ordinance to Determine Tar Color which is Usable for Medicaments and the like" and allowed for use in coloring medicaments, quasi-drugs and cosmetics and which does not have a harmful effect to the human body, can be used. For example, Red No. 3 (erythrosine), Red No. 102 (new coccin), Red No. 106 (acid red), Red No. 201 (lithol rubine B), Red No. 227 (fast acid magenta), Red No. 230 (1) (erytrosine YS), Red No. 203 (2) (erythrosine YSK), Red No. 231 (phloxine BK), Red No. 232 (rose bengal K), Red No. 401 (violamine R), Red No. 502 (ponceau 3R), Red No. 503 (ponceau R), Red No. 504 (ponceau SX), Red No. 506 (fast red S), Yellow No. 202 (2) (uranine K), Yellow No. 4 (tartrazine), Yellow No. 402 (polar yellow 5G), Yellow No. 403 (1) (naphthol yellow S), Yellow No. 406 (metanil yellow), Green No. 3 (fast green FCF), Green No. 201 (alizanine cyanine green F), Green No. 204 (pyrine conc), Green No. 205 (light green SF yellowish), Green No. 401 (naphthol green B), Green No. 402 (guinea green B), Blue No.1 (brilliant blue FCF), Blue No. 2 (indigo carmine), Blue No. 202 (patent blue NA), Blue No. 205 (alfazurine FG), Brown No. 201 (resorcine brown), Purple No. 401 (alizurol purple), Black No. 401 (naphthol blue black), and the like can be used.

Pigments used in the present invention include an organic, inorganic and lake pigments.

Examples of organic pigments include an organic dye such as β-carotene, carthamin or cochineal, in addition to azo, indigo and phthalocyanine pigments.

Examples of inorganic pigments include an extender pigment such as mica, talc or kaolin, a white pigment such as titanium dioxide or zinc oxide, a pearl pigment such as titanium mica or fish scale flake, and a specific functional pigment such as boron nitride, a photochromic pigment, synthetic mica or hybrid fine powder, in addition to a coloring pigment such as red iron oxide, yellow iron oxide, black iron oxide, chromium oxide, ultramarine, iron blue and carbon black.

Examples of lake pigments include a dye lake pigment such as aluminium lake, in addition to a lake pigment such as Red Nos. 202, 204, 206, 207 or 220.

Although a compounding amount of the copolymer in the cosmetic in accordance with the present invention is not restricted, it is preferably 0.1 to 10 wt % and, more preferably, 1 to 5 wt %. When the compounding amount is too low, a sufficient effect can not be obtained with one treatment. On the contrary, applicability, spreadability and the like become poor and flaking may occur when the compounding amount is too high.

A compounding amount of the pigment and acidic dye can be properly determined according to the required colorability and it is not restricted. However, the compounding amount is usually 0.01 to 20 wt % and, preferably, 0.1 to 10 wt %. Secondary adhesion occurs easily when the pigment or dye is too high.

A cosmetic preparation in accordance with the present invention can be, for example, in addition to a hair colorant such as a colorant spray, a color crayon or a color mousse, a make-up cosmetic such as a nail enamel, a mascara or an eyebrow make-up.

The effects when the other film-forming ingredients were used in a cosmetic which used the copolymer and a pigment and/or an acidic dye were studied. As for a film-forming ingredient, siliconized pullulan (substitution degree 1.7, molecular weight of pullulan as a staring material about 200,000) was used.

EXAMPLE 3-4

Prescription 3-3 (Temporary hair colorant):

| | |
|---|---|
| Copolymer | 5 wt % |
| Siliconized pullulan | 1 |
| Carbon black | 1 |
| Ethanol | 22.8 |
| Light isoparaffin | 70 |
| Silicone rubber | 0.2 |
| Perfume | q.s. |
| Antiseptic | q.s. |

A temporary hair colorant was prepared according to the above-mentioned prescription 3-3. Also, a hair colorant, which used ethanol instead of siliconized pullulan, was prepared as a control. The test was conducted by the following method by using each hair colorant as a sample.

(Color retention)

Each sample was applied to white hair and left on for 3 minutes. Then the hair was washed with water and dried naturally. Thereafter, the hair was washed with a commercially available shampoo and dried naturally every day. The color retention after 10 days was evaluated by visual inspection. The evaluation standard is as follows.

⊚: Very good as compared to the control.
○: Equal to or slightly good as compared to the control.
Δ: Slightly inferior as compared to the control.
X: Inferior as compared to the control.
(Smoothness)

Smoothness at 1st and 10th days of the above color retention test was evaluated by touch. The evaluation standard is as follows.

⊚: Very good as compared to the control.
○: Equal to or slightly good as compared to the control.
Δ: Slightly inferior as compared to the control.
X: Inferior as compared to the control.
(Flaking on repeated applications)

Flaking was evaluated in the same way as the method of the above Test Example 1-4.

TABLE 22

| Copolymer | Monomer (wt %) | | | | Color Reten-tion | Smoothness | | Flaking on Repeated Applications |
|---|---|---|---|---|---|---|---|---|
| | A2 | B1 | C* | D1 | | 1st | 10th | |
| 3-19 | 60 | 35 | 5(C3) | 20 | ⊚ | ⊚ | ⊚ | ⊚ |
| 3-20 | 50 | 40 | 10(C1) | — | ○ | ⊚ | ⊚ | ⊚ |
| 3-21 | 50 | 25 | 25(C2) | — | ○ | ⊚ | ⊚ | ⊚ |
| 3-22 | 67 | 37 | — | — | ○ | ⊚ | ⊚ | ⊚ |
| 3-23 | 50 | — | 50(C3) | — | ○ | ⊚ | ⊚ | ⊚ |

As shown in TABLE 22, when siliconized pullulan was used together with the copolymer, the color retention can be made equal to or better than the case where only the copolymer was used. The touch also can be made smoother as compared to the case of using the copolymer only, and in particular, the effect with respect to the damaged hair is remarkable. These effects were maintained even when shampooing was repeated. Further, although flaking on repeated applications might occur when only the copolymer was used, it could be inhibited by using siliconized pullulan together with the copolymer. The effect was the same for the acidic hair colorants.

TABLE 23

| Ingredient | Amount | | | | | | | |
|---|---|---|---|---|---|---|---|---|
| Copolymer 3-19 | 5 | 5 | 5 | 2 | 2 | 1 | 0.1 | — |
| Siliconized pullulan | — | 0.1 | 0.5 | 0.5 | 2 | 5 | 5 | 5 |
| Color Retention | — | ○ | ⊚ | ⊚ | ⊚ | ○ | Δ | Δ |
| Smoothness | | | | | | | | |
| 1st day | — | ○ | ⊚ | ⊚ | ⊚ | ⊚ | ⊚ | ⊚ |
| 10th day | — | ○ | ⊚ | ⊚ | ⊚ | ⊚ | ⊚ | ⊚ |
| Flaking on Repeated Applications | Δ | ⊚ | ⊚ | ⊚ | ⊚ | ⊚ | ⊚ | ⊚ |

TABLE 23 shows the results of a test which was conducted in the same way as Test Example 3-4 after changing the ratio of the copolymer and siliconized pullulan. The amount of the copolymer and pullulan were adjusted with ethanol.

The color retention tends to be lower when the copolymer is low. On the other hand, the color retention and smoothness are not sufficiently improved and flaking on repeated applications may occur when siliconized pullulan is low. Accordingly, the ratio between the copolymer and siliconized pullulan is preferably 100:1 and, more preferably, 50:1–1:1 by weight.

As described above, by using the copolymer containing reactive silyl groups and a siliconized polysaccharide together with a pigment and/or an acidic dye, a cosmetic having favorable color retention and feel of use and low flaking on repeated applications can be obtained.

When only the siliconized polysaccharide was used, the color retention was low as compared to when only the copolymer was used. Therefore, these effects are improved by using the siliconized polysaccharide together with the copolymer. This is because at the time of forming the cross-linked coating the siliconized polysaccharide is included into the coating, and the cross-linked coating and the siliconized polysaccharide act synergistically.

Examples 3-1 to 3-3 Colorant Spray

The test was conducted in the same manner as the above Test Example 3-1 by using the colorant sprays of TABLE 24. Every example had high resistance to washing and was excellent in the color retention as compared to Comparative Example 3-1.

TABLE 24

| Ingredient | Example 3-1 | Example 3-2 | Example 3-3 | Comp. Ex. 3-1 |
|---|---|---|---|---|
| (1) Copolymer 3-4 | 1 | 3 | 5 | — |
| (2) Polyvinylpyrrolidone/ vinyl acetate copolymer | — | — | — | 5 |
| (3) Black iron oxide | 1 | 1 | 1 | 1 |
| (4) Ethanol | 46 | 44 | 42 | 42 |
| (5) POE (40) hydrogenated castor oil | 1 | 1 | 1 | 1 |
| (6) Octyl palmitate | 1 | 1 | 1 | 1 |
| (7) LPG (3.5 kg/cm$^2$ at 20° C.) | 50 | 50 | 50 | 50 |
| (8) Perfume | q.s. | q.s. | q.s. | q.s. |
| Color retention | ○ | ⊚ | ⊚ | X |

(Manufacturing Process)

The ingredients (1) to (6) and (8) were stirred and uniformly mixed. The mixture was filled into an aerosol container and then the ingredient (7) was placed in the container to obtain a colorant spray.

Examples 3-4 to 3-6 Hair Mist Applicator

The test was conducted in the same manner as the above Test Example 3-1 by using the hair mist applicators of TABLE 25. Every example had high resistance to washing and was excellent in the color retention as compared to Comparative Example 3-2.

TABLE 25

| Ingredient | Example 3-4 | Example 3-5 | Example 3-6 | Comp. Ex. 3-2 |
|---|---|---|---|---|
| (1) Copolymer 3-1 | 1 | 3 | 5 | — |
| (2) Polyvinylalcohol/ vinyl acetate copolymer | — | — | — | 5 |
| (3) Carbon black | 1 | 1 | 1 | 1 |
| (4) Ethanol | 96 | 94 | 92 | 92 |
| (5) POE (9) laurylether | 1 | 1 | 1 | 1 |
| (6) Dimethylpolysiloxane (5 cps) | 1 | 1 | 1 | 1 |
| (7) Perfume | q.s. | q.s. | q.s. | q.s. |
| Color retention | ○ | ○ | ⊚ | X |

(Manufacturing Process)

The ingredients (1) to (7) were stirred and uniformly mixed. The mixture was filled into a container, thereby obtaining a hair mist applicator.

Examples 3-7 to 3-9 Colorant Spray

The test was conducted in the same manner as the above Test Example 3-1 by using the colorant sprays of TABLE 26.

Every example had high resistance to washing and was excellent in the color retention as compared to Comparative Example 3-3.

TABLE 26

| Ingredient | Example 3-7 | Example 3-8 | Example 3-9 | Comp. Ex. 3-3 |
|---|---|---|---|---|
| (1) Copolymer 3-5 | 1 | 3 | 5 | — |
| (2) Polyvinylpyrrolidone/ vinyl acetate copolymer | — | — | — | 5 |
| (3) Resorcine brown | 1 | 1 | 1 | 1 |
| (4) Ethanol | 48.2 | 46.2 | 44.2 | 49.2 |
| (5) Benzyl alcohol | 5 | 5 | 5 | 5 |
| (6) Citric acid | 0.3 | 0.3 | 0.3 | 0.3 |
| (7) POE (100) hydrogenated castor oil | 1 | 1 | 1 | 1 |
| (8) Highly polymerized dimethylpolysiloxane | 0.5 | 0.5 | 0.5 | 0.5 |
| (9) Dimethyl polysiloxane (5 cps) | 3 | 3 | 3 | 3 |
| (10) LPG (3.5 kg/cm$^2$ at 20° C.) | 40 | 40 | 40 | 40 |
| (11) Perfume | q.s. | q.s. | q.s. | q.s. |
| Color retention | ⊚ | ⊚ | ⊚ | Δ |

(Manufacturing Process)

The ingredients (1) to (9) and (11) were stirred and uniformly mixed. The mixture was filled into an aerosol container and then the ingredient (10) was placed in the container to obtain a colorant spray.

Example 3-10 Nail Enamel

Nail enamels were prepared according to the following prescription 3-4 by using the foregoing Copolymers 3-1 to 3-6. The prepared nail enamel was applied on the nails of female panelists. After drying, the nails were washed with water. Thereafter, the nails were observed in daily Cracking or peeling was observed within 3 days when ethanol was used instead of the copolymer. However, cracking or peeling was absolutely not observed for 7 days or more and the color retention was maintained when the copolymer was used.

| Prescription 3-4: | |
|---|---|
| Nitrocellulose | 10 wt % |
| Alkyd resin | 10 |
| Acetyltributyl citrate | 5 |
| Ethyl acetate | 10 |
| Butyl acetate | 5 |
| Copolymer | 5 |
| Ethanol | 55 |
| Rhodamine B | q.s. |
| Suspending agent | q.s. |

(Manufacturing Process)

Rhodamine B was added to a part of alkyd resin and a part of acetyltributyl citrate and the mixture was sufficiently kneaded. The other ingredients were mixed and dissolved and the former mixture was added thereto to form the entire mixture. The entire mixture was uniformly dispersed to obtain a nail enamel.

Example 3-11 Mascara

Mascaras were prepared according to the following prescription 3-5 by using the above Copolymers 3-1 to 3-6. Each mascara was applied on eyelashes and was washed with water after drying. Thereafter, the eyelashes were washed with a commercially available detergent and dried repeatedly.

As a result, as shown in TABLE 27, impairment of the color was clearly prevented and the color retention was improved by using the copolymer.

| Prescription 3-5: | |
|---|---|
| Black iron oxide | 10 wt % |
| Solid paraffin | 5 |
| Lanolin wax | 5 |
| Light isoparaffin | 5 |
| Ethanol | 70 |
| Copolymer | 5 |
| Perfume | q.s. |

(Manufacturing Process)

Each ingredient was mixed successively and uniformly dispersed to obtain a mascara.

TABLE 27

| Copolymer | Color Retention* |
|---|---|
| Copolymer 3-1 | ○ |
| Copolymer 3-2 | ⊚ |
| Copolymer 3-3 | ⊚ |
| Copolymer 3-4 | ⊚ |
| Copolymer 3-5 | ⊚ |
| Copolymer 3-6 | ⊚ |
| Nothing (control) | X |

*Evaluation standard of color retention:
⊚ . . . Color was impaired by washing 5 times or more.
○ . . . Color was impaired by washing 3 times or more.
X . . . Color was impaired by washing once.

Examples 3-12 to 3-14 Colorant Spray

The test was conducted in the same manner as the above Test Example 3-1 by using the colorant sprays of TABLE 28. Every example had high resistance to washing and was excellent in the color retention as compared to Comparative Example 3-4. Also, the feeling of use was smooth.

TABLE 28

| Ingredient | Example 3-12 | Example 3-13 | Example 3-14 | Comp. Ex. 3-4 |
|---|---|---|---|---|
| (1) Copolymer 3-9 | 1 | — | — | — |
| (2) Copolymer 3-11 | — | 1 | — | — |
| (3) Copolymer 3-12 | — | — | 1 | — |
| (4) Polyvinylpyrrolidone/ vinyl acetate copolymer | — | — | — | 1 |
| (5) Black iron oxide | 1 | 1 | 1 | 1 |
| (6) Ethanol | 46 | 46 | 46 | 46 |
| (7) POE (40) hydrogenated castor oil | 1 | 1 | 1 | 1 |
| (8) Octyl palmitate | 1 | 1 | 1 | 1 |
| (9) LPG (3.5 kg/cm$^2$ at 20° C.) | 50 | 50 | 50 | 50 |
| (10) Perfume | q.s. | q.s. | q.s. | q.s. |
| Color Retention | ⊚ | ⊚ | ⊚ | X |
| Smoothness | ⊚ | ⊚ | ⊚ | X |

(Manufacturing process)

The ingredients (1) to (8) and (10) were stirred and mixed uniformly. Then the mixture and the ingredient (9) were filled into an aerosol container, successively, to obtain a colorant spray.

Examples 3-15 to 3-17 Hair Mist Applicator

The test had been conducted in the same manner as the above-mentioned Test Example 3-1 by using the hair mist applicators of TABLE 29. Every example had high resistance to washing to be excellent in color retention as compared to Comparative Example 3-5. Also, feeling of use thereof was smooth.

TABLE 29

| Ingredient | Example 3-15 | Example 3-16 | Example 3-17 | Comp. Ex. 3-5 |
|---|---|---|---|---|
| (1) Copolymer 3-8 | 1 | — | — | — |
| (2) Copolymer 3-9 | — | 1 | — | — |
| (3) Copolymer 3-13 | — | — | 1 | — |
| (4) Polyvinylalcohol vinyl acetate copolymer | — | — | — | 5 |
| (5) Carbon black | 1 | 1 | 1 | 1 |
| (6) Ethanol | 96 | 96 | 96 | 96 |
| (7) POE (9) laurylether | 1 | 1 | 1 | 1 |
| (8) Dimethylpolysiloxane (5 cps) | 1 | 1 | 1 | 1 |
| (9) Perfume | q.s. | q.s. | q.s. | q.s. |
| Color Retention | ⊚ | ⊚ | ⊚ | X |
| Smoothness | ⊚ | ⊚ | ⊚ | X |

(Manufacturing process)

The ingredients (1) to (9) were stirred and uniformly mixed. The mixture was filled into a container, thereby obtaining a hair mist applicator.

Examples 3-18 to 3-20 Colorant Spray

The test was conducted in the same manner as the above Test Example 3-1 by using the colorant sprays of TABLE 30. Every example had high resistance to washing and was excellent in the color retention as compared to Comparative Example 3-6.

TABLE 30

| Ingredient | Example 3-18 | Example 3-19 | Example 3-20 | Comp. Ex. 3-6 |
|---|---|---|---|---|
| (1) Copolymer 3-11 | 1 | — | — | — |
| (2) Copolymer 3-13 | — | 1 | — | — |
| (3) Copolymer 3-14 | — | — | 1 | — |
| (4) Polyvinylpyrrolidone/vinyl acetate copolymer | — | — | — | 1 |
| (5) Resorcine brown | 1 | 1 | 1 | 1 |
| (6) Ethanol | 48.2 | 48.2 | 48.2 | 48.2 |
| (7) Benzyl alcohol | 5 | 5 | 5 | 5 |
| (8) Citric acid | 0.3 | 0.3 | 0.3 | 0.3 |
| (9) POE (100) hydrogenated castor oil | 1 | 1 | 1 | 1 |
| (10) Highly polymerized dimethylpolysiloxane | 0.5 | 0.5 | 0.5 | 0.5 |
| (11) Dimethyl polysiloxane (5 cps) | 3 | 3 | 3 | 3 |
| (12) LPG (3.5 kg/cm$^2$ at 20° C.) | 40 | 40 | 40 | 40 |
| (13) Perfume | q.s. | q.s. | q.s. | q.s. |
| Color Retention | ⊚ | ⊚ | ⊚ | X |
| Smoothness | ⊚ | ⊚ | ⊚ | X |

(Manufacturing Process)

The ingredients (1) to (11) and (13) were stirred and uniformly mixed. The mixture was filled into an aerosol container and then the ingredient (12) was placed in the container to obtain a colorant spray.

Example 3-21 Nail Enamel

Nail enamels were prepared according to the following prescription 3-6 by using the above Copolymers 3-11, 12 and 14. The nail enamel was applied on the nails of female panelists. After drying, the nails were washed with water. Thereafter, the nails were observed in daily. Cracking or peeling was observed within 3 days when ethanol was used instead of the copolymer. However, cracking or peeling was absolutely not observed for 10 days or more and the color retention was maintained when the copolymer was used.

| Prescription 3-6: | |
|---|---|
| Nitrocellulose | 10 wt % |
| Alkyd resin | 10 |
| Acetyltriethyl citrate | 5 |
| Ethyl acetate | 10 |
| Butyl acetate | 5 |
| Copolymer | 5 |
| Ethanol | 55 |
| Rhodamine B | q.s. |
| Suspending agent | q.s. |

(Manufacturing process)

Rhodamine B was added to a part of alkyd resin and a part of acetyl triethyl citrate and the first mixture was fully kneaded. The other ingredients were then mixed and dissolved, and the first mixture was added thereto to an entire mixture. The entire mixture was uniformly dispersed to obtain a nail enamel.

Example 3-22

The copolymers 3-24 to 3-26 were synthesized according to the following method and tested in the same way as the above Test Example 3-1. As a result, every copolymer had high color retention and favorable feeling of use as shown in TABLE 31. Also, flaking was not observed with each copolymer.

Copolymer 3-24

12.0g of Monomer A2 and 6.0 g of Monomer B1 were dissolved in 100 ml of ethanol and the solution was stirred while heating under a nitrogen gas stream for 1 hour at 70° C. 0.05 g of dimethyl 2,2'-azobis(isobutyrate) was added to the solution and the mixture was reacted over night The reaction mixture was cooled to room temperature and concentrated under a vacuum. The residue was dissolved in 10 ml of ethanol and the solution was added to 500 ml of n-hexane. The deposits were collected to obtain the copolymer.

Copolymer 3-25

In a similar manner to Copolymer 3-24, except for using 10.0 g of Monomer A2, 2.0 g of Monomer B1, and 1.0 g of Monomer D1, the copolymer was obtained.

Copolymer 3-26

In a similar manner to Copolymer 3-24, except for using 10.0 g of Monomer A2, 10.0 g of Monomer C4, and 0.5 g of Monomer D1, the copolymer was obtained.

TABLE 31

Acidic hair colorant (prescription 3-2, Copolymer 2 wt %)

| | Monomer (wt %) | | | | Color | | |
|---|---|---|---|---|---|---|---|
| Copolymer | A2 | B1 | C4 | D1 | Retention | Smoothness | Texture |
| 3-24 | 67 | — | — | 33 | ○ | ○ | ⊚ |
| 3-25 | 77 | 15 | — | 8 | ⊚ | ○ | ⊚ |
| 3-26 | 49 | — | 49 | 2 | ⊚ | ⊚ | ⊚ |

EXAMPLE 3-23

Colorant Spray

| | |
|---|---|
| Red iron oxide | 1 wt % |
| Copolymer 3-19 | 4 |
| Siliconized pullulan | 1 |
| Silicone rubber | 0.2 |
| Light isoparaffin | 70 |
| Ethanol | 23.8 |
| Perfume | q.s. |
| Antiseptic | q.s. |

(Manufacturing Process)

After silicone rubber and siliconized pullulan were dissolved in light isoparaffin, a stock solution of a spray was prepared by adding an ethanol solution of Copolymer 3-19 and the other ingredients to the former solution. 70 parts of the stock solution was filled into a can and a valve was mounted. 30 parts of dimethyl ether gas was filled into the can to obtain a colorant spray.

The colorant spray had favorable color retention and the feeling of use and inhibited flaking on repeated applications as compared to the colorant spray that did not use siliconized pullulan.

EXAMPLE 3-24

Nail Enamel

| | |
|---|---|
| Pigment | 2 wt % |
| Copolymer 3-22 | 7 |
| Siliconized pullulan | 0.5 |
| Light isoparaffin | 45 |
| Ethanol | 45.5 |
| Perfume | q.s. |
| Antiseptic | q.s. |

(Manufacturing Process)

After siliconized pullulan was dissolved in light isoparaffin, a ethanol solution of Copolymer 3-22 and the other ingredients were added to the solution, thereby obtaining a nail enamel.

The nail enamel had favorable color retention and feeling of use and inhibited flaking on repeated applications as compared to the nail enamel that did not use siliconized pullulan.

EXAMPLE 3-25

Oily Water-Proof Mascara

| | |
|---|---|
| Iron oxide | 10 wt % |
| Copolymer 3-20 | 2 |
| Siliconized pullulan | 2 |
| Light isoparaffin | 50 |
| Ethanol | 20 |
| Solid paraffin | 5 |
| Lanolin wax | 5 |
| Glycerine | 6 |
| Perfume | q.s. |
| Antioxidant | q.s. |

(Manufacturing Process)

After siliconized pullulan, solid paraffin and lanolin wax were dissolved in light isoparaffin, a ethanol solution of Copolymer 3-20 and a glycerin dispersion of iron oxide was added to the mixture to obtain a mascara.

The mascara had favorable color retention and feeling of use and inhibited flaking on repeated applications as compared to the mascara that did not use siliconized pullulan.

<Cosmetic Packs>

Presently, various packs (masks) which remove wastes of sebum, the old horny layer, dirt or the like have been developed in the field of cosmetics.

Such cosmetic packs are classified broadly into: (1) a peel-off type which is a paste or jelly and used by peeling off a coating which is formed after applying and drying; (2) a type which is removed by wiping or washing down after applying; (3) a type where a pack composition is adhered to a sheet such as a nonwoven fabric sheet and the sheet is peeled off after patching; or the like. A cosmetic pack which mainly cleans the skin is almost the peel-off type or patching type.

In these cosmetic packs, in addition to skin-cleaning action, strippability where the pack coating is completely peeled off without remaining on the skin, is required. Also, in the peel-off type pack, stretchability of the cosmetic pack on the skin and coating strength are also important.

However, the pack, which sufficiently satisfies consumers in this respect has not yet been obtained. Namely, in the cosmetic packs of peel-off type or patching type, there is a limit of their adhesiveness to the skin and a limit to removal activity of wastes of sebum or the old horny layer, because they have to be peeled off later.

Therefore, the effects when the copolymer containing reactive silyl groups was used into such peel-off type cosmetic pack.

Test Example 4-1 i) Synthesis of Copolymer

Copolymer 4-1

12.0 g of 3-methacryloxypropyltrimethoxysilane (Monomer A1) and 8.0 g of methyl methacrylate (Monomer B1) were dissolved in 100 ml of ethanol and the solution was stirred while heating under a nitrogen gas stream for 1 hour at 70° C. 0.05 g of potassium persulfate was added to the solution and the mixture was reacted over night. The reaction mixture was cooled to room temperature and concentrated under a vacuum. The residue was dissolved in 10 ml of ethanol and the mixture was added to 500 ml of n-hexane. The deposits were collected to obtain the copolymer.

In the NMR spectral data (solvent CDCl3 or DMSO-d6) of the resulting copolymer, a signal of hydrogen atom in CH2=C of the monomers used as starting materials was not observed at or near 6–7 ppm. As a result, generation of copolymer was confirmed. Also, in the present invention, generation of the other copolymers were confirmed in a similar manner.

Copolymer 4-2

In a similar manner to the synthesis of Copolymer 1, except for using 10.0 g of Monomer A1, 2.0 g of Monomer B1 and 8.0 g of 3-methacryloxypropyl(trimethylsiloxy)silane (Monomer C3), the copolymer was obtained.

Copolymer 4-3

In a similar manner to the synthesis of Copolymer 1, except for using 12.0 g of Monomer A1, 5.0 g of Monomer B1 and 3.0 g of 3-methacryloxypropyldimethylpolysiloxane (Monomer C1), the copolymer was obtained.

Copolymer 4-4

In a similar manner to the synthesis of Copolymer 1, except for using 12.0 g of Monomer A1, 7.0 g of Monomer B1 and 1.0 g of Monomer C2, the copolymer was obtained.

ii) Preparation of Sample

Oil phase (first agent):

| | |
|---|---|
| Polyvinyl acetate | 15 wt % |
| Polyvinyl alcohol | 10 |
| Sorbitol | 5 |
| PEG 400 | 5 |
| Liquid isoparaffin | 2 |
| Squalane | 2 |
| POE sorbitan monostearate | 1 |
| Ethanol | 10 |
| Copolymer | 10 |

Water phase (second agent):

| | |
|---|---|
| Titanium dioxide | 5 |
| Talc | 10 |
| Purified water | 25 |

(Manufacturing Process)

The first and second agents were prepared by sufficiently mixing components of oil phase and water phase separately. A control wherein the copolymer was not used (wherein, 35 wt % of purified water was used) was also prepared.

iii) Test Method

The first and second agents were mixed just before the test. The mixture was applied on the face. After drying naturally, the pack preparation was peeled off. 20 professional panelists evaluated their feelings with respect to applicability, strippability, coating strength and skin-cleaning effect. The evaluation standard was as follows.

◎: 15 or more answered favorable.
○: 10 to 14 answered favorable.
Δ: 5 to 9 answered favorable.
X: 4 or less answered favorable.

TABLE 32

| Copolymer (constituent monomer) | Applicability | Strippability | Coating Strength | Cleaning Effect |
|---|---|---|---|---|
| No copolymer (control) | Δ | Δ | Δ | Δ |
| Copolymer 4-1 (A1-B1) | Δ | ○ | ◎ | ◎ |
| Copolymer 4-2 (A1-B1-C3) | ◎ | ◎ | ◎ | ◎ |
| Copolymer 4-3 (A1-B1-C1) | ○ | ◎ | ◎ | ◎ |
| Copolymer 4-4 (A1-B1-C2) | ○ | ◎ | ◎ | ◎ |

As shown in TABLE 32, the cosmetic pack comprising any of Copolymers 1 to 4 having Monomers (A) and (B) as a constituent monomer had extremely high coating strength and skin-cleaning effect and was excellent in strippability, as compared to when these copolymers were not used. In particular, applicability and strippability can be further improved without loss of coating strength and skin-cleaning effect, when the copolymer having Monomers (A) to (C) are used. Also, the coating of the pack became flexible when the copolymer was used Monomer (C).

TABLE 33

| Monomer composition of copolymer (A1)/(B1) (wt %) | Coating Strength | Cleaning Effect |
|---|---|---|
| 10/90 | Δ | Δ |
| 25/75 | ○ | ○ |
| 40/60 | ◎ | ◎ |
| 60/40 | ◎ | ◎ |
| 85/15 | ◎ | ◎ |
| 96/4 | ○ | ○ |
| 100/0 | Δ | Δ |

TABLE 33 shows the results when the test was conducted in the same way as the above Test Example 4-1 with a change of the monomer composition of the copolymer.

As shown in TABLE 33, the cosmetic pack using a copolymer consisting of Monomers (A) and (B) can form a strong pack coating on the skin to exhibit high skin-cleaning effect. However, these effects are not sufficient when the percentage of Monomer (A) in the copolymer is too low or too high. Accordingly, the percentage of Monomer (A) in the copolymer is 25 to 99 wt % and, preferably, 40 to 85 wt %.

TABLE 34

| Monomer Composition of Copolymer (A1)/(B1)/(C3) (wt %) | Applicability | Strippability | Cleaning Effect |
|---|---|---|---|
| 60/40/0 | Δ | ○ | ◎ |
| 60/35/5 | ○ | ◎ | ◎ |
| 60/25/15 | ◎ | ◎ | ◎ |
| 50/10/40 | ◎ | ◎ | ◎ |

As shown in TABLE 34, usability such as applicability or strippability can be improved without a loss of skin-cleaning effect by introducing Monomer (C) into the copolymer consisting of Monomers (A) and (B). The percentage of Monomer (C) in the copolymer is 1 wt % or more and, preferably, 5 wt % or more.

TABLE 35

| Amount of Copolymer | Applicability | Strippability | Coating Strength | Cleaning Effect |
|---|---|---|---|---|
| 1 wt % | Δ | Δ | Δ | Δ |
| 5 | ○ | ○ | ○ | ○ |
| 10 | ◎ | ◎ | ◎ | ◎ |
| 20 | ◎ | ◎ | ◎ | ◎ |
| 50 | ◎ | ◎ | ◎ | ◎ |

TABLE 35 shows the results when the amount of the copolymer is changed in the cosmetic pack using the Copolymer 42. The increase and decrease of the amount of the copolymer were adjusted with purified water.

As shown in TABLE 35, the skin-cleaning effect is not sufficiently exhibited and applicability, strippability and coating strength are also deteriorated when the amount of the copolymer in the cosmetic pack is too low. On the contrary, applicability or strippability tends to be lower when the amount is too high. Therefore, the amount of the copolymer in the cosmetic pack is 5 to 50 wt % and, preferably, 10 to 20 wt %.

When the copolymer containing reactive silyl groups is used in the cosmetic pack, and a coating formed by cross-linking with hydrolyzing the copolymer on the skin is peeled off the skin after drying, wastes of sebum, the old horny layer and dirt of the skin are completely removed with the pack coating and the feeling of use is favorable. Also, this pack coating does not tear on peeling, and it can be peeled off completely.

This effect can be obtained because due to hydrolyzing after applying the cosmetic pack using the copolymer, the cross-linked copolymer is strongly and uniformly coated on surface of the skin in a network state by cross-linking on the body portion to which it is applied to form the strong pack coating.

Preferred examples of the copolymer used to the cosmetic pack in the present invention include the copolymer shown by Formula (IX) above.

As a monomer composition of the copolymer, the percentage of Monomer (A) in the copolymer is preferably 25 to 99 wt % and, more preferably, 40 to 85 wt %. When the percentage of Monomer (A) is too low, the skin-cleaning effect is not sufficiently exhibited, since the part for the cross-linking reaction is low. On the other hand, skin-cleaning effect tends to be deteriorated when the percentage of Monomer (A) is too high. This results because the cross-linking reaction does not progress neatly and a large amount of the unreacted part remains on the cross-linked copolymer because the part for the cross-linking reaction is too high. Also, flexibility of the cross-linked coating may be deteriorated to be inferior in usability.

Monomer (1) adjusts the ratio of Monomer (A). Also, since the copolymer consisting of Monomers (A) and (C) is too sticky and is difficult to use, Monomer (B) which can inhibit such stickiness and adjust the nature of the coating can be added. The percentage of Monomer (B) is preferably 1 wt % or more and, more preferably, 15 wt % or more in the copolymer. When the percentage of Monomer (B) is too high, the percentages of the other monomers are decreased and the copolymer has poor solubility against alcohol type solvents. Therefore, the percentage of Monomer (B) is preferably 75 wt % or less and, more preferably, 60 wt % or less.

Monomer (C) has a siloxane part and gives the coating plasticity. Also, Monomer (C) contributes to applicability, flexibility of the coating, strippability or the like. The percentage of Monomer (C) is preferably 1 wt % or more and, more preferably, 5 wt % or more in the copolymer of the present invention. However, when the percentage of Monomer (C) is too high, the percentages of the other monomers become relatively low and the skin-cleaning effect tends to be deteriorated. Therefore, the percentage of Monomer (C) is 74 wt % or less and, preferably, 60 wt % or less.

In the cosmetic pack of the present invention, the concentration of the copolymer is not restricted. However, the concentration of the copolymer in the final composition is preferably 5 to 50 wt % and, more preferably, 10 to 20 wt %. When the amount is too low, a sufficient effect can not be obtained. On the contrary, applicability, feeling of use and the like may become inferior when the amount is too high.

A method for applying a cosmetic pack in accordance with the present invention is characterized in that the cosmetic pack is hydrolyzed on the skin to cross-link molecules of the copolymer and then the formed pack coating is peeled off after drying. As a method for drying, natural drying is usually used. Though a method for cross-linking is described in the foregoing, it is preferable that the copolymer is mixed with water, acid or alkali and then the mixture be applied immediately. This can improve strippability.

A preferred example of the cosmetic pack of the present invention can be a cosmetic pack using plural agents. An example of such cosmetic pack includes a two-agent type cosmetic pack using a first agent which is a non-aqueous composition containing the copolymer and a second agent which is an aqueous composition containing water. As a method for treating a person with the cosmetic pack, it is preferable to mix the first and the second agents immediately before application and then to peel off the pack after application and drying. Strippability is favorable when the two-agent type cosmetic pack is used. It is possible to mix an optional composition excluding the first and second agents in the present invention. Also, a final mixture of the plural-agent type cosmetic pack is within the scope of the present invention.

The type of the cosmetic pack of the present invention is called a peel-off type or patching type, which is peeled off after application. The preparation form can be various formulations such as solubilization type, dispersion type or emulsion type. A property of the cosmetic pack can be made liquid, paste, jelly, gel or the like. Also, a sheet type pack can be made by applying the cosmetic pack on a sheet of nonwoven fabric or the like.

The other ingredients that are generally used in cosmetic packs or other cosmetics, can be used in the cosmetic pack of the present invention as long as the effect of the present invention is not spoiled. For example, in addition to surfactants, pH adjustors, antiseptics, antioxidants, chelating agents, thickening agents, film-forming ingredients, oily components, highly polymerized compounds, humectants, powders, coloring matters and the like, drugs such as whitening agents or germicidal agents can be used.

In particular, plasticity or strippability of the coating can be improved by an oily component, silicone rubber or the other polymers, or clay mineral. Also, strippability can be improved by a powder.

<Application for Other Materials To Be Treated>

The copolymer of the present invention has an excellent coating-forming property and resistance to washing. Accordingly, effect with respect to the material except for the hair or skin, e.g., fibers, paper, glass and the like were studied.

Test Example 5-1

First, the test was conducted according to the following method so as to investigate the effect on fibers.

(Water-repellency)

A 5% ethanol solution of each copolymer was sprayed on a cotton shirt and the shirt was dried naturally. A few drops of water were dropped onto the shirt and its water-repellency was evaluated with visually. Washing the shirt with a washing machine by using a commercially available household detergent and drying naturally was repeated 10 times. Thereafter, water-repellency was evaluated in the same way as above.

Evaluation standard

⊚: Extremely favorable

○: Favorable

Δ: Slightly unfavorable

X: Unfavorable (Smoothness)

2 g of 5% ethanol solution of each copolymer was applied on 10 g of a sheet of cotton fabric and dried naturally. Smoothness of this fabric was evaluated by 20 professional panelists by touch.

Evaluation standard

⊚: 15 or more answered favorable.

○: 10 to 14 answered favorable.

Δ: 5 to 9 answered favorable.

X: 4 or less answered favorable.

(Suitability as a sizing)

A 5% ethanol solution of the tested copolymer was sprayed on a cotton shirt and was hardened by ironing with a steam iron. Immediately after ironing, the shirt was evaluated by touch. Further, suitability as a sizing after washing and drying 10 times in a manner similar to the water-repellency test above was evaluated.

Evaluation standard

⊚: Extremely favorable.

○: Favorable.

Δ: Slightly unfavorable.

X: Unfavorable.

(Crease-smoothing property/crease resistance)

In a similar manner to the above-mentioned suitability as a sizing test, the state of a crease was judged after ironing, and washing and drying 10 times with visually. Thereby, the crease-smoothing property/crease resistance was evaluated.

Evaluation standard

⊚: Extremely favorable.

○: Favorable.

Δ: Slightly unfavorable.

X: Unfavorable.

(Resistance to fouling)

A drop of coffee was dropped onto a shirt that was treated in the same way as the above water-repellency test The attachment degree of the fouling coffee after wiping the drop with another fabric was judged with visually. Thereby, the resistance to fouling was evaluated.

Evaluation standard

⊚: Extremely favorable

○: Favorable

Δ: Slightly unfavorable

X: Unfavorable (Texture)

A 2 g of 5% ethanol solution of each copolymer was applied on 10 g of a sheet of cotton fabric and dried naturally. The texture of this fabric was evaluated by 20 professional panelists by touch.

Evaluation standard

⊚: 15 or more answered favorable.

○: 10 to 14 answered favorable.

Δ: 5 to 9 answered favorable.

X: 4 or less answered favorable.

TABLE 36

| Copolymer | Monomer (wt %) | | Water-repellency | | Resistance to Fouling | Smoothness |
| | A2 | B1 | just after treatment | after washing | | |
|---|---|---|---|---|---|---|
| 5-1 | 20 | 80 | ○ | X | ○ | Δ |
| 5-2 | 33 | 67 | ○ | ○ | ○ | Δ |
| 5-3 | 50 | 50 | ○ | ○ | ○ | Δ |
| 5-4 | 67 | 33 | ○ | ○ | ○ | Δ |
| 5-5 | 83 | 17 | ○ | Δ | ○ | Δ |
| 5-6 | 100 | 0 | Δ | X | Δ | X |
| Untreated | — | — | X | X | X | X |

As shown in TABLE 36, the cross-linked coating formed by the copolymer using only Monomers (A) and (B) can provide favorable water-repellency and resistance to fouling. The resistance to washing was not sufficient and the effect could not be retained when Monomer (A) in the copolymer was too low. On the contrary, the water-repellency, the resistance to washing and the resistance to fouling tend to deteriorate when Monomer (A) is 100%. Also, the feeling of use was inferior and flaking occurred. Accordingly, the percentage of Monomer (A) is preferably 25 to 85 wt % and, more preferably, 40 to 75 wt % in the copolymer.

Next, the copolymer having Monomers (C) and (D) along with Monomers (A) and (B) was tested.

TABLE 37

| Copolymer | Monomer (wt %) | | | Water-repellency | | Resistance to Fouling | Smoothness |
| | A2 | B1 | C2 | just after treatment | after washing | | |
|---|---|---|---|---|---|---|---|
| 5-7 | 10 | 40 | 50 | ○ | X | ○ | ⊚ |
| 5-8 | 20 | 40 | 40 | ○ | X | ⊚ | ⊚ |
| 5-9 | 45 | 50 | 5 | ⊚ | ⊚ | ⊚ | ⊚ |
| 5-10 | 50 | 25 | 25 | ⊚ | ⊚ | ⊚ | ⊚ |
| 5-11 | 50 | 10 | 40 | ⊚ | ⊚ | ⊚ | ⊚ |
| 5-12 | 55.6 | 33.3 | 11.1 | ⊚ | ⊚ | ⊚ | ⊚ |
| 5-13 | 60 | 35 | 5 | ⊚ | ⊚ | ⊚ | ⊚ |
| 5-14 | 71.4 | 14.3 | 14.3 | ⊚ | ⊚ | ⊚ | ⊚ |
| 5-15 | 85 | 10 | 5 | ○ | Δ | ○ | ⊚ |

As shown in TABLES 36 and 37, when the copolymer using Monomers (A) to (C) are used for treatment, the water-repellency, the resistance to washing and the resistance to fouling can be considerably improved as compared to the copolymer using only Monomers (A) and (B). Also, the treated shirts were very smooth and the results ware extremely favorable. The percentage of Monomer (C) in the copolymer is 1 wt % or more and, preferably, 5 wt % or more.

Copolymer 5-16 using only Monomers (A) and (C) has stickiness. It was shown that the presence of Monomer (B) inhibited stickiness caused by Monomer (C) and gave a moderate nature to the coating. The percentage of Monomer (B) in the copolymer is 5 wt % or more and, preferably, 10 wt % or more.

TABLE 38

| Copolymer | Monomer (wt %) | | | Water-repellency | | Resistance to Fouling | Smoothness |
| | A2 | B1 | C* | just after treatment | after washing | | |
|---|---|---|---|---|---|---|---|
| 5-16 | 50 | 10 | 40(C1) | ⊚ | ⊚ | ⊚ | ⊚ |
| 5-17 | 60 | 35 | 5(C3) | ⊚ | ⊚ | ⊚ | ⊚ |
| 5-18 | 60 | 35 | 5(C4) | ⊚ | ⊚ | ⊚ | ⊚ |
| 5-19 | 50 | 25 | 25(C4) | ⊚ | ○ | ⊚ | ⊚ |

*The inside of ( ) represents Monomer (C) used.

As shown in TABLE 38, even when Monomer (C) in the copolymer was Monomer C1, C3 or C4, the same effect could be obtained as when Monomer (C) is Monomer C2 (see TABLE 37).

TABLE 39

| Copolymer | Monomer (parts by weight) | | | | | Water-repellency | | Texture |
| | A1 | B1 | C3 | C4 | D1 | just after treatment | after washing | |
|---|---|---|---|---|---|---|---|---|
| 5-17 | 60 | 35 | 5 | — | — | ⊚ | ⊚ | Δ |
| 5-18 | 60 | 35 | — | 5 | — | ⊚ | ⊚ | Δ |
| 5-20 | 60 | 35 | 5 | — | 10 | ⊚ | ⊚ | ⊚ |
| 5-21 | 60 | 35 | — | 5 | 10 | ⊚ | ○ | ⊚ |
| 5-22 | 60 | 35 | — | 5 | 20 | ⊚ | ○ | ⊚ |
| 5-23 | 60 | 35 | — | 5 | 50 | ○ | ○ | ⊚ |
| 5-24 | 60 | 35 | — | 5 | 100 | Δ | x | ⊚ |

As shown in TABLE 39, the cross-linked coating of the copolymer using Monomers (A) to (D) can give fibers good texture and moisture touch. When Monomer (D) is too high, the water-repellency and the resistance to washing tend to deteriorate because the hydrophilic property of the crosslinked coating becomes high. Accordingly, the percentage of Monomer (D) is 1 to 100 wt % and, preferably, 5 to 50 wt % with respect to the combined amount of Monomers (A) to (C) in the copolymer.

TABLE 40

| | Copolymer | | | | | |
|---|---|---|---|---|---|---|
| | 5-10 | 5-16 | 5-17 | 5-19 | 5-21 | Untreated |
| Suitability as a Sizing | | | | | | |
| (just after treatment) | ◉ | ◉ | ◉ | ◉ | ◉ | X |
| (after washing) | ◉ | ◉ | ◉ | ○ | ○ | X |
| Crease-smoothing property/crease resistance | | | | | | |
| (just after ironing) | ◉ | ◉ | ◉ | ◉ | ◉ | X |
| (after washing) | ◉ | ○ | ◉ | ○ | ○ | X |

As shown in TABLE 40, the cross-linked coating of the copolymer in accordance with the present invention exhibits an excellent suitability as a sizing and gives a crease-smoothing property/crease resistance with respect to fiber.

TABLE 41

| | Copolymer | | | | | |
|---|---|---|---|---|---|---|
| | 5-10 | 5-16 | 5-17 | 5-19 | 5-21 | Untreated |
| Water-repellency (just after treatment) | ◉ | ◉ | ◉ | ◉ | ◉ | X |
| Resistance to Fouling | ◉ | ◉ | ◉ | ◉ | ◉ | X |

TABLE 41 shows the result of a water-repellency test and a resistance to fouling test conducted in the same way by using paper instead of a cotton shirt. The result shows that high water-repellency and resistance to fouling can be obtained when the copolymer of the present invention is used to treat paper.

TABLE 42

| | Copolymer | | | | | |
|---|---|---|---|---|---|---|
| | 5-10 | 5-16 | 5-17 | 5-19 | 5-21 | Untreated |
| Angle of contact | 96.0 | 96.4 | 92.0 | 97.0 | 94.6 | 9.7 |
| Angle of inclination | 13.0 | 11.0 | 14.2 | 15.0 | 13.8 | —* |

*Impossible to measure because a waterdrop remained.

TABLE 42 is the result obtained when the hydrophobic degree of glass was investigated by using a glass plate in the place of a cotton shirt and by treating the glass in a manner similar to the above water-repellency test. The hydrophobic degree was evaluated by the angles of contact and inclination of the water. A drop of water was dropped onto a glass and the angle of water contact was measured. Also, the angle of inclination was measured as the angle of a glass which was gradually inclined to an angle where the waterdrop just started to move. A large angle of contact and a small angle of inclination indicate a large hydrophobic degree.

As a result, the glass plate treated with the copolymer in accordance with the present invention has very large angle of water contact as compared to the untreated glass plate. On the other hand, the angle of inclination is very small. Accordingly, it was shown that the copolymer of the present invention can give the glass plate a very high hydrophobic ability.

As shown above, the copolymer of the present invention formed the cross-linked coating which was excellent in water-repellency and resistance to fouling by a cross-linking reaction on the treated material. Also, the coating is very hard to remove and exhibits these effects exhibit continuously even after water or detergent cleaning. Accordingly, the copolymer can be used as a water-repellent or a stain proofing agent for various materials. Also, the copolymer of the present invention is preferable as a treatment for fibers such as water-repellents for fibers, sizing for fibers or a crease-resistant agent because the cross-linked coating has very little flaking. When the copolymer is used to treat fibers, the cross-linked coating has suitability as a sizing, crease-resistance, and a very excellent feeling of use.

A preferable example of the copolymer used for such a water-repellent or other treatment of fibers can be shown by Formula (IX) or (X).

As a monomer composition of the copolymer, the percentage of Monomer (A) in the copolymer is preferably 25 to 85 wt % and, more preferably, 40 to 75 wt %. When the percentage of Monomer (A) is too low, the effect such as water-repellency or resistance to washing may not be sufficiently exhibited since the part for the cross-linking reaction is low. On the contrary, water-repellency or resistance to washing tends to deteriorate when the percentage of Monomer (A) is too high. This is because the cross-linking reaction does not progress neatly and a large amount of the unreacted part remains on the cross-linked copolymer because the part for the cross-linking reaction is too high. Also, the feeling of use may be worse and flaking may be caused.

Monomer (B) contributes to water-repellency of the cross-linked coating. Also, Monomer (B) adjusts the nature of the cross-linked coating which inhibits flaking and stickiness caused by Monomer (C). The percentage of Monomer (B) is 5 wt % or more and, preferably, 10 wt % or more in the copolymer. When the percentage of Monomer (B) is too high, the percentages of other monomers are decreased and the copolymer tends to have poor solubility against alcohol type solvents. Therefore, the percentage of Monomer (B) is 75 wt % or less and, preferably, 60 wt % or less.

Monomer (C) has a siloxane part. Accordingly, Monomer (C) can remarkably improve water-repellency of the cross-linked coating and give fibers smoothness to make the result favorable. Monomer (C) also inhibits flaking. The percentage of Monomer (C) is 1 wt % or more and, preferably, 5 wt % or more in the copolymer of the present invention. However, when the percentage of Monomer (C) is too high, the percentages of the other monomers become relatively low and resistance to washing tends to be poor. Therefore, the percentage of Monomer (C) is 70 wt % or less and, preferably, 60 wt % or less.

Also, when the copolymer, which uses Monomer (D) together with Monomers (A) to (C) as constituent monomers, is treated, smoothness and good texture can be given to fibers and a moist feeling of use can be obtained. However, when Monomer (D) is too high, the water-repellency, resistance to washing and the like are inferior because the hydrophilic nature of the coating becomes high because of the amine portion contained in Monomer (D). The percentage of Monomer (D) is 1 to 100 wt % and, preferably, 5 to 50 wt % with respect to the combined amount of Monomers (A) to (C).

Although a concentration of the copolymer is not restricted in particular, it is preferably 0.1 to 10 wt % and, more preferably, 1 to 5 wt %. When the amount of the copolymer is too low, a sufficient effect can not be obtained with one treatment. On the contrary, applicability, spreadability, the feeling of use and the like become inferior and flaking may be caused when the amount is too high.

The other ingredients can be used in the water-repellent or treatment for fibers of the present invention within a range that the effect of the present invention is not spoiled. Also, it is possible to form a colored coating having a water-repellency when coloring materials such as a pigment or a dye are used therein. On the other hand, it is possible to prevent discoloring of the material to be treated when an ultraviolet absorber is used therein.

As for the material to be treated with the water-repellent and treatment for fibers of the present invention, fibrous materials having optional forms such as single fiber, spun yarn, random fiber, fabric and a final product are preferable. The final product can be, for example, shoes, an umbrella, a hat or cap, a ski suit, a shirt or a carpet. In the present invention, the fibrous material also includes leather, the other fibrous materials and products thereof such as fiber of paper or paper products. Also, in addition to the fibrous material, it is possible to treat the other materials such as glass plates, glass products, metal plates or metal products, where water-repellency and resistance to fouling are required.

As a method for applying the water-repellent and treatment for fibers of the present invention, known methods, e.g., dipping methods, roll coating methods or spray methods, may be used. Of course, instruments such as brush or comb can be used as occasion demands.

One of the most simple treatment methods in the present invention can be, for example, a method where the material to be treated is dipped into or sprayed with a solution of the copolymer of the present invention and then the material is, optionally with squeezing, dried naturally or with heating. Also, in clothes such as shirts, a method where a solution of the copolymer is sprayed on the cloth before ironing and then the cloth is pressed by iron or steam iron, is preferable.

Lastly, a synthetic example of the copolymer in accordance with the present invention is described.

Synthetic Examples 1 to 24

Monomers (A) to (D) were mixed the ratios described in TABLE 43, and then the preparation amount of the mixture was dissolved in 100 ml of ethanol. The solution was heated while stirring under a nitrogen gas stream for 1 hour at 70° C. 0.05 g of potassium persulfate was added to the solution and the mixture was reacted overnight. The reaction mixture was cooled to room temperature and concentrated under a vacuum. The residue was dissolved in 10 ml of ethanol and the solution was added to 500 ml of n-hexane. The deposits were collected to give the copolymer.

TABLE 43

| Synthetic Examples | A2 | B1 | C1 | C2 | C3 | C4 | D1 | Preparation Amount (g) | Yield (%) |
|---|---|---|---|---|---|---|---|---|---|
| 1 | 5 | 1 | 4 | — | — | — | — | 20 | 97.5 |
| 2 | 5 | 1 | 2 | — | — | — | — | 16 | 96.9 |
| 3 | 5 | 1 | — | 4 | — | — | — | 20 | 98.5 |
| 4 | 5 | 1 | — | 1 | — | — | — | 14 | 100.0 |
| 5 | 5 | 3 | — | 1 | — | — | — | 18 | 98.9 |
| 6 | 12 | 7 | — | 1 | — | — | — | 20 | 97.5 |
| 7 | 9 | 10 | — | 1 | — | — | — | 20 | 92.5 |
| 8 | 2 | 1 | — | 1 | — | — | — | 20 | 98.5 |
| 9 | 5 | 1 | — | — | 4 | — | — | 20 | 99.0 |
| 10 | 12 | 7 | — | — | 1 | — | — | 20 | 97.0 |
| 11 | 9 | 10 | — | — | 1 | — | — | 20 | 95.0 |
| 12 | 5 | 1 | — | — | — | 4 | — | 20 | 99.0 |
| 13 | 5 | 3 | — | — | — | 1 | — | 20 | 97.5 |
| 14 | 12 | 7 | — | — | — | 1 | — | 20 | 98.5 |
| 15 | 9 | 10 | — | — | — | 1 | — | 20 | 94.5 |
| 16 | 2 | 1 | — | — | — | 1 | — | 20 | 97.5 |
| 17 | 12 | 7 | — | — | 1 | 2 | — | 20 | 97.0 |
| 18 | 12 | 7 | — | — | — | 1 | 2 | 20 | 99.5 |
| 19 | 12 | 7 | — | — | — | 1 | 4 | 22 | 90.9 |
| 20 | 12 | 2 | — | — | — | 6 | 2 | 22 | 91.4 |
| 21 | 12 | 2 | — | — | — | 6 | 4 | 24 | 96.7 |
| 22 | 12 | 4 | — | — | — | 4 | 2 | 22 | 90.0 |
| 23 | 12 | 4 | — | — | — | 4 | 4 | 24 | 91.3 |
| 24 | 4 | 8 | — | 8 | — | — | — | 20 | 91.0 |

FIGS. 2 to 5 each show NMR spectral data of the copolymer which was obtained by Synthetic Examples 6, 10, 12 and 18, respectively. In these NMR spectral data (solvent CDCl3 or DMSO-d6) of the resulting copolymer, the signal of hydrogen atom in of the monomers used as starting materials was not observed at or near 6–7 ppm. As a result, generation of the copolymer was confirmed. Also, in the present invention, generation of the other copolymers was confirmed in a similar manner.

Synthetic Example 25

10.00 g of Monomer A1 and 2.02 g of Monomer B1 were dissolved in 100 ml of ethanol and the solution was heated while stirring under a nitrogen gas stream for 1 hour at 70° C. 0.05 g of dimethyl 2,2-azobis(isobutyrate) was added to the solution and the mixture was heated while stirring for 24 hours at 70° C. The reaction mixture was cooled to room temperature and concentrated under a vacuum. The residue was dissolved in 10 ml of ethanol and the solution was added to 500 ml of n-hexane. The deposits were collected to give 11.50 g (yield 95.7%) of the copolymer.

Synthetic Example 26

10.00 g of Monomer A2 and 5.00 g of ethyl methacrylate were dissolved in 100 ml of ethanol and the solution was heated while stirring under a nitrogen gas stream for 1 hour at 70° C. 0.05 g of 2,2-azobisisobutyronitrile was added to the solution and the mixture was heated while stirring for 24 hours at 70° C. The reaction mixture was cooled to room temperature and was concentrated under a vacuum. The residue was dissolved in 10 ml of ethanol and the solution was added to 500 ml of n-hexane. The deposits were collected to give 14.20 g (yield 94.7%) of the copolymer.

Synthetic Example 27

18.95 g (yield 94.8%) of the copolymer was obtained by the same process as in Synthetic Example 25, except for using 10.00 g of Monomer A1 and 10.00 g of Monomer B1.

What is claimed is:

1. A composition comprising a silyl-containing copolymer wherein said copolymer comprises:

(a) Monomer (A) shown by the following Formula (I):

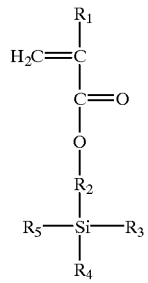

Formula (I)

as a silyl-containing monomer and wherein $R_1$, is a hydrogen atom or methyl group; $R_2$ is an alkylene group having 1–6 carbon atoms; and $R_3$, $R_4$ and $R_5$ each is a reactive functional group which can cross-link molecules of the copolymer by hydrolyzing;

(b) Monomer (B) shown by the following Formula (II):

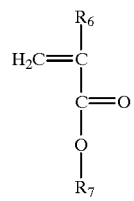

Formula (II)

wherein $R_6$ is a hydrogen atom or methyl group; $R_7$ is an alkyl group having 1–18 carbon atoms;

(c) Monomer (C) shown by the following Formula III:

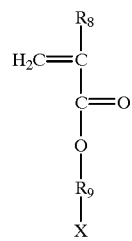

Formula (III)

wherein $R_8$ is a hydrogen atom or methyl group; $R_9$ is an alkylene group having 1–6 carbon atoms; and X is a group expressed by any of the following Formulae (IV) to (VI):

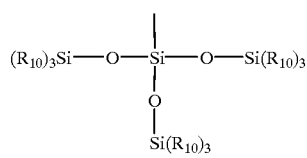

Formula (IV)

wherein $R_{10}$ is an alkyl group having 1–6 carbon atoms;

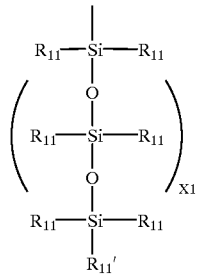

Formula (V)

wherein $R_{11}$ and $R_{11'}$ each is an alkyl group having 1–6 carbon atoms; and X1 is an integer of positive number; and

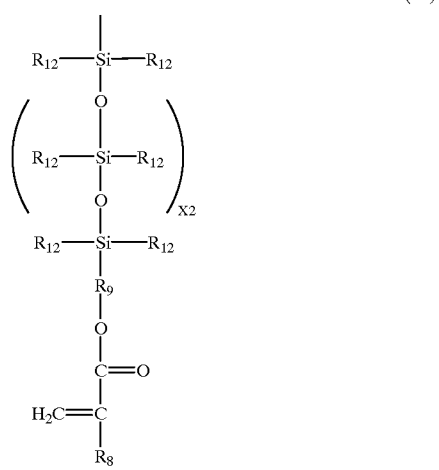

Formula (VI)

wherein $R_8$ and $R_9$ are the same as defined in Formula (III); $R_{12}$ is an alkyl group having 1–6 carbon atoms; and X2 is and integer of positive number; and (d) Monomer (D) shown by the following Formula (VII):

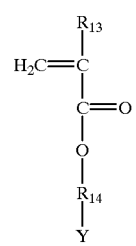

Formula (VII)

wherein $R_{13}$ is a hydrogen atom or methyl group; $R_{14}$ is an alkylene group having 1–6 carbon atoms; and y is a group expressed by $-N^+(R_{15})_3$ or $-N(R_{15})_2$, wherein $R_{15}$ is an alkyl group having 1–6 carbon atoms;

and wherein the percentage of Monomer (A) is at least about 25 wt % of the copolymer.

2. A composition according to claim 1, wherein the percentage of Monomer (B) is 1 wt % or more in the copolymer.

3. A composition according to claim 1, wherein the percentage of Monomer (C) is 1 wt % or more in the copolymer.

4. A composition according to claim 1, wherein the percentage of Monomer (D) is within the range of 1 to 100 wt % with respect to the combined weight of Monomer (A), Monomer (B) and Monomer (C) in the copolymer.

5. A composition wherein each of $R_3$, $R_4$, and $R_5$ is an alkoxy group having 1–6 carbon atoms.

6. A cosmetic for coating, which is the composition according to claim 1.

7. A cosmetic for modifying the nature of hair, which is the composition according to claim 1.

8. A composition according to claim 1, which is a hair colorant further comprising a pigment and/or an acidic dye.

9. A composition according to claim 1, which is a cosmetic further comprising a pigment and/or an acidic dye.

10. A composition according to claim 1, which is a make-up cosmetic further comprising a pigment and/or acidic dye.

11. A cosmetic preparation according to claim 6, additionally comprising a siliconized polysaccharide.

12. A composition according to claim 1, which is a cosmetic pack.

13. A composition according to claim 1, wherein said composition is a water-repellent.

14. A composition according to claim 13, wherein the percentage of Monomer (A) is 25 to 85 wt % in the copolymer.

15. A composition according to claim 13, wherein the percentages of Monomer (B) and (C) are 5 or 1 wt % or more, respectively, in the copolymer.

16. A composition according to claim 1, wherein said composition is a treatment for fibers.

17. A composition according to claim 16, wherein the percentage of Monomer (A) is from about 25 to about 85 wt % in the copolymer.

18. A composition according to claim 16, wherein the percentages of Monomer (B) and Monomer (C) are 5 wt % or more and 1 wt % or more in the copolymer, respectively.

19. A copolymer according to claim 2, wherein each of R3, R4 and R5 is an alkoxy group having 1–6 carbon atoms.

20. A coating-forming method comprising a step of cross-linking the molecules of the copolymer of the composition of claim 1 by hydrolyzing said composition on material to be treated with it.

21. A coating-forming method according to claim 20, wherein said composition is the cosmetic and the material to be treated is human hair or epidermis.

22. A coating-forming method according to claim 20, wherein said composition is the water-repellent and the material to be treated is fibers, paper or glass.

23. A coating-forming method according to claim 20, wherein said composition is the treatment for fibers and the material is to be treated is fibers.

24. A method for applying a cosmetic pack comprising steps of hydrolyzing the cosmetic pack of claim 12 on skin to cross-link molecules of the copolymer, and peeling the cosmetic pack from the skin after drying.

* * * * *